United States Patent [19]
Lai et al.

[11] Patent Number: 6,093,743
[45] Date of Patent: Jul. 25, 2000

[54] THERAPEUTIC METHODS EMPLOYING DISULFIDE DERIVATIVES OF DITHIOCARBAMATES AND COMPOSITIONS USEFUL THEREFOR

[75] Inventors: Ching-San Lai, Encinitas; Vassil Vassilev, San Diego, both of Calif.

[73] Assignee: Medinox Inc., San Diego, Calif.

[21] Appl. No.: 09/103,639

[22] Filed: Jun. 23, 1998

[51] Int. Cl.$^7$ .................... A61K 31/16; A61K 31/095; A61K 31/105

[52] U.S. Cl. .................... 514/599; 514/706; 514/707; 514/851; 514/861; 514/863; 514/866; 514/909; 514/912

[58] Field of Search .................... 514/599, 706, 514/707, 851, 861, 863, 866, 909, 912

[56] References Cited

U.S. PATENT DOCUMENTS

| | | | |
|---|---|---|---|
| 4,160,452 | 7/1979 | Theeuwes | 128/260 |
| 4,256,108 | 3/1981 | Theeuwes | 128/260 |
| 4,265,874 | 5/1981 | Bonsen et al. | 424/15 |
| 5,206,264 | 4/1993 | Marangos | 514/483 |
| 5,358,703 | 10/1994 | Lai | 424/9 |
| 5,373,021 | 12/1994 | Marangos | 514/483 |
| 5,741,815 | 4/1998 | Lai | 514/492 |
| 5,747,532 | 5/1998 | Lai | 514/491 |
| 5,756,540 | 5/1998 | Lai | 514/492 |
| 5,847,004 | 12/1998 | Lai | 514/599 |
| 5,877,203 | 3/1999 | Medford et al. | 514/423 |

FOREIGN PATENT DOCUMENTS

| | | | |
|---|---|---|---|
| WO 97/18805 | 5/1997 | WIPO | A61K 31/325 |
| WO 97/32585 | 9/1997 | WIPO | A61K 31/495 |

OTHER PUBLICATIONS

Aisaka et al., "N$^G$–Methylarginine, an Inhibitor of Endothelium–Derived Nitric Oxide Synthesis, is a Potent Pressor Agent in the Guinea Pig: Does Nitric Oxide Regulate Blood Pressure in Vivo?" *Biochemical and Biophysical Research Communications*, 160(2):881–886 (1989).

Atkinson et al., "Cyclosporine–Associated Central Nervous System Toxicity After Allogeneic Bone Marrow Transplantation," *Transplantation*, 38(1):34–37 (1984).

Bredt and Snyder, "Nitric Oxide: A Physiologic Messenger Molecule," *Annu. Rev. Biochem*, 63:175–95 (1994).

Diket et al., "Nitric oxide inhibition causes intrauterine growth retardation and hind–limb disruptions in rats," *Am. J Obstet Gynecol*, 171(5):1243–1250 (1994).

Glauser et al., "Pathogenesis and Potential Strategies for Prevention and Treatment of Septic Shock: An Update," *Clinical Infectious Diseases*, 18(2):S205–16 (1994).

Harbrecht et al., "Inhibition of nitric oxide synthesis during endotoxemia promotes intrahepatic thrombosis and an oxygen radical–mediated hepatic injury," *Journal of Leukocyte Biology*, 52:390–394 (1992).

Henderson et al., "The Effects of Nitric Oxide Inhibition on Regional Hemodynamics During Hyperdynamic Endotoxemia," *Arch. Surg.* 129:1271–1275 (1994).

Hibbs et al., "Evidence for Cytokine–inducible Nitric Oxide Synthesis from L–Arginine in Patients Receiving Interleukin–2 Therapy," *J. Clin. Invest.*, 89:867–877 (1992).

Ignarro, Louis J., "Biosynthesis and Metabolism of Endothelium–Derived Nitric Oxide," *Annu. Rev. Pharmacol. Toxicol.*, 30:535–60 (1990).

Ignarro et al., "Endothelium–derived relaxing factor produced and released from artery and vein is nitric oxide," *Proc. Natl. Acad. Sci. USA*, 84:9265–9269 (1987).

Kim et al., "Loss and Degradation of Enzyme–bound Heme Induced by Cellular Nitric Oxide Synthesis," *Journal of Biological Chemistry*, 270(11):5710–5713 (1995).

Komarov et al., "In Vivo Spin Trapping of Nitric Oxide in Mice," *Biochemical and Biophysical Research Communications*, 195(3):1191–1198 (1993).

Komarov and Lai, "Detection of nitric oxide production in mice by spin–trapping electron paramagnetic resonance spectroscopy," *Biochimica et Biophysica Acta*, 1272:29–36 (1995).

Lai and Komarov, "Spin trapping of nitric oxide produced in vivo in septic–shock mice," *FEBS Letters*, 345:120–124 (1994).

Lowenstein and Snyder, "Nitric Oxide, A Novel Biologic Messenger," *Cell*, 70:705–707 (1992).

Luss et al., "Inhibition of Nitric Oxide Synthesis Enhances the Expression of Inducible Nitric Oxide Synthase mRNA and Protein in a Model of Chronic Liver Inflammation," *Biochemical and Biophysical Research Communications*, 204(2):635–640 (1994).

Miles et al., "Association between biosynthesis of nitric oxide and changes in immunological and vascular parameters in patients treated with interleukin–2," *European Journal of Chemical Investigation*, 24:287–290 (1994).

(List continued on next page.)

*Primary Examiner*—Kevin E. Weddington
*Attorney, Agent, or Firm*—Gary Cary Ware & Freidenrich; Stephen E. Reiter; Shelia R. Kirschenbaum

[57] ABSTRACT

The present invention provides a novel dithiocarbamate disulfide dimer useful in various therapeutic treatments, either alone or in combination with other active agents. In one method, the disulfide derivative of a dithiocarbamate is coadministered with an agent that inactivates (or inhibits the production of) species that induce the expression of nitric oxide synthase to reduce the production of such species, while, at the same time reducing nitric oxide levels in the subject. In another embodiment, free iron ion levels are reduced in a subject by administration of a disulfide derivative of a dithiocarbamate(s) to scavenge free iron ions, for example, in subjects undergoing anthracycline chemotherapy. In another embodiment, cyanide levels are reduced in a subject by administration of a disulfide derivative of a dithiocarbamate so as to bind cyanide in the subject. In a further aspect, the present invention relates to compositions and formulations useful in such therapeutic methods.

51 Claims, 5 Drawing Sheets

OTHER PUBLICATIONS

Minnard et al., "Inhibition of Nitric Oxide Synthesis Is Detrimental During Endotoxemia," *Arch. Surg.,* 129:142–148 (1994).

Mitaka et al., "Effects of nitric oxide synthase inhibitor on hemodynamic change and $O_2$ delivery in septic dogs," *Inhibitor of No Synthase and Endotoxin Shock,* H2017–H2020 (1995).

Moncada and Higgs, "The L–Arginine–Nitric Oxide Pathway," *The New England Journal of Medicine,* 329(27):2002–2012 (1993).

Nieper et al., "The development and examination of fungistatic compounds for cancer treatment" Aerztl. Forsh., 16:I/523–I/540 (1962).

Richard M. J. Palmer, "The Discovery of Nitric Oxide in the Vessel Wall," *Arch. Surg.,* 128:396–401 (1993).

Palmer et al. "Nitric oxide release accounts for the biological activity of endothelium–derived relaxing factor," *Nature,* 327:524–526 (1987).

Radomski and Moncada, "Regulation of Vascular Homeostasis by Nitric Oxide" *Thrombosis and Haemostasis,* 70(1):36–41 (1993).

Rees et al., "Role of endothelium–derived nitric oxide in the regulation of blood pressure," *Proc. Natl. Acad. Sci. USA.,* 86:3375–3378 (1989).

Robertson et al., "Detrimental Hemodynamic Effects of Nitric Oxide Synthase Inhibition in Septic Shock," *Arch Surg* 129:149–156 (1994).

Rodeberg et al., "Nitric Oxide: An Overview," *The American Journal of Surgery,* 170:292–303 (1995).

Shinobu et al., "Sodium N–Methyl–D–glucamine Dithiocarbamate and Cadmium Intoxication," *Acta pharmacol, et toxicol,* 54:189–194 (1984).

Statman et al., "Nitric Oxide Inhibition in the Treatment of the Sepsis Syndrome Is Detrimental to Tissue Oxygenation," *Journal of Surgical Research,* 57(1):93–98 (1994).

St. John and Dorinsky, "Immunologic Therapy for ARDS, Septic Shock and Multiple–Organ Failure," *Chest,* 103:932–943 (1993).

Waage et al., "Cytokine mediators of septic infections in the normal and granulocytopenic host," *Eur J Haematol.,* 50:243–249 (1993).

Winlaw et al., "Urinary Nitrate Excretion is a Noninvasive Indicator of Acute Cardiac Allograft Rejection and Nitric Oxide Production in the Rat," *Transplantation,* 58(9):1031–1036 (1994).

Yang et al., "Induction of Myocardial Nitric Oxide Synthase by Cardiac Allograft Rejection," *J. Clin. Invest.,* 94:714–721 (1994).

THERAPEUTIC METHODS EMPLOYING DISULFIDE DERIVATIVES OF DITHIOCARBAMATES AND COMPOSITIONS USEFUL THEREFOR

FIELD OF THE INVENTION

The present invention relates to therapeutic methods employing dithiocarbamates to reduce the level of species associated with disease states in mammals. In one aspect, the invention relates to compositions containing disulfide derivatives of dithiocarbamates and to therapeutic methods employing such compositions.

BACKGROUND OF THE INVENTION

In 1987, nitric oxide (.NO), a gaseous free-radical, was discovered in humans (see, for example, Ignarro et al., in *Proc. Natl. Acad. Sci.*, USA 84:9265–69 (1987) and Palmer et al., in *Nature* 327:524–26 (1987)). As an indication of the significance of this discovery for the understanding of human physiology and pathophysiology, Science magazine selected nitric oxide as the molecule of the year in 1992.

Nitric oxide is formed from the terminal guanidino nitrogen atom of L-arginine by nitric oxide synthase (NOS; see, for example, Rodeberg et al., in *Am. J. Surg.* 170:292–303 (1995), and Bredt and Snyder in *Ann. Rev. Biochem.* 63:175–95 (1994)). Two major forms of nitric oxide synthase, constitutive and inducible enzymes, have been identified.

Under physiological conditions, a low output of .NO is produced by the constitutive, calcium-dependent NOS isoform (cNOS) present in numerous cells, including endothelium and neurons. This low level of nitric oxide is involved in a variety of regulatory processes, e.g., blood vessel homeostasis, neuronal communication and immune system function. On the other hand, under pathophysiological conditions, a high output of .NO is produced by the inducible, calcium-independent NOS isoform (iNOS) which is expressed in numerous cell types, including endothelial cells, smooth muscle cells and macrophages. These high levels of nitric oxide have been shown to be the etiology of endotoxin shock. This high output of .NO further contributes to inflammation-related tissue damage, neuronal pathology, N-nitrosamine-induced carcinogenesis and mutations in human cells and bacteria via deamination reaction with DNA. Nitric oxide can therefore be seen to be a mixed blessing, being very desirable when present in small amounts, while potentially being highly detrimental when produced in excessive quantities.

Nitric oxide is a potent vasodilator (see, for example, Palmer in *Arch. Surg.* 128:396–401 (1993) and Radomski & Moncada in *Thromb. Haemos.* 70:36–41 (1993). For example, in blood, .NO produced by the endothelium diffuses isotropically in all directions into adjacent tissues. As .NO diffuses into the vascular smooth muscle, it binds to guanylate cyclase enzyme, which catalyzes the production of cGMP, inducing vasodilation (see, for example, Ignarro, L. J., *Ann. Rev. Toxicol.* 30:535–560 (1990); Moncada, S., *Acta Physiol. Scand.* 145:201–227 (1992); and Lowenstein and Snyder, *Cell* 70:705–707 (1992)). The overproduction of nitric oxide causes an extreme drop in blood pressure, resulting in insufficient tissue perfusion and organ failure, syndromes that are associated with many diseases and/or conditions (e.g., septic shock, overexpression of cytokines, allograft rejection, and the like). The overproduction of nitric oxide is triggered by a number of stimuli, such as, the overproduction of inflammatory cytokines (e.g., tumor necrosis factor (TNF), interleukin-1 (IL-1), interferons, endotoxin, and the like). Additionally, the overproduction of .NO has been discovered to be one of the major side-effects of cytokine therapy (see, for example, Miles et al., in *Eur. J. Clin. Invest.* 24:287–290 (1994) and Hibbs et al., in *J. Clin. Invest.* 89:867–877 (1992)). Thus, abnormally elevated nitric oxide levels have been linked to many inflammatory and infectious diseases.

Inflammatory cytokines (e.g., TNF, interleukins or interferons) and infectious agents (e.g., endotoxin) induce nitric oxide overproduction by inducing transcription of the inducible nitric oxide synthase gene, leading to the production of inducible nitric oxide synthase, which in turn results in the overproduction of nitric oxide. The production of nitric oxide by the above-described pathway can be disrupted in a variety of ways. Thus, for example, there have been attempts to develop monoclonal antibodies (e.g., anti-endotoxin antibodies, anti-cytokine antibodies, anti-cytokine receptor antibodies, and the like) in efforts to block the .NO production pathway at the transcriptional level. Unfortunately, however, such efforts have met with very limited success (see, for example, Glauser et al., in *Clin. Infect. Dis.* 18:S205–16 (1994) and St. John & Dorinsky, in *Chest* 103:932–943 (1993)). At least one reason for the relative lack of success in the art is the fact that the production of inflammatory cytokines is short-lived (see, for example, Wange & Steinsham in *Eur. J. Haematol.* 50:243–249 (1993)), while overproduction of nitric oxide lasts several days, causing systemic hypotension, insufficient tissue perfusion and organ failure.

Thus, for example, during endotoxemia, TNF production peaks at about 1–2 hours. Therefore, in order to be effective, anti-TNF antibodies would have to be administered at an early stage after infection. Indeed, in many clinical settings, patients are likely to already have been infected with bacteria prior to being admitted. Accordingly, such therapeutic methods have met with only limited success.

Currently, many pharmaceutical companies have turned their attention to the design and development of substrate or product analogue inhibitors of the enzyme, NOS, in efforts to treat the overproduction of .NO. However, recent data show that the inhibition of NOS is detrimental to subjects. For example, rodent studies show that inhibition of the production of nitric oxide causes intrauterine growth retardation and hind-limb disruptions in rats (see, for example, Diket et al., in *Am. J. Obstet. Gynecol.* 171:1243–1250 (1994)). Furthermore, the inhibition of nitric oxide synthesis during endotoxemia has also been shown to be detrimental (see, for example, C. O. Corso et al., J. Hepatol. 28:61–69, 1998; K. Kaneda et al. Acta Anaesthesiol. Scand. 42:399–405, 1988; R. I. Cohen, et al. Crit. Care Med. 26:738–747, 1998. Similar results have been reported in larger animal studies, such as dogs and swine (see, for example, Statman et al., in *J. Surg. Res.* 57:93–98 (1994); Mitaka et al., *Am. J. Physiol.* 268:H2017–H2023(1994); Robertson, et al., *Arch. Surg.* 129:149–156 (1994); and Henderson et al., *Arch. Surg.* 129:1271–1275 (1994)).

Dithiocarbamates such as pyrrolidine dithiocarbamate have been determined to be potent inhibitors of nuclear factor kappa B (NFκB) in intact cells (see, for example, R. Schreck et al., in *J. Exp Med* 175:1181–1194 (1992). In addition, NFκB has also been shown to up-regulate the expression of cell adhesive molecules, including the vascular cell adhesive molecule-1 (VCAM-1; see, for example, M. F. Iademarco et al., *J. Biol Chem* 267:16323–16329 (1992)). Interestingly, in view of these known inhibitory effects of dithiocarbamates on NFκB, and the known ability of NFκB to induce expression of VCAM-1, Medford et al. propose the allegedly new use of dithiocarbamates to treat cardiovascular diseases mediated by VCAM-1, through the inhibition of the NFκB pathway (see U.S. Pat. No. 5,380, 747).

It is also beneficial to remove cyanide (CN), a fast acting toxic compound, from subjects exposed thereto. Cyanide is frequently used in suicides, homicide, and chemical warfare (see, for example, Salkowski et al., in Vet. Hum. Toxicol. 36:455–466 (1994) and Borowitz et al., in B. Somani (Ed.), Chemical Warfare Agents, Academic Press, New York, pp. 209–236 (1992)). Cyanide toxicity can arise from a variety of sources, e.g., from inhalation of smoke produced by the pyrolysis of plastics or nitrile-based polymer fibers, materials that are commonly used in construction and for furniture manufacture. Cyanide toxicity can also occur from ingestion of plant extracts containing cyanogenic glycosides (such as cassava), or from inhalation of airborne vapors encountered in industrial or occupational settings (for example, during electroplating). Clinically, the release of cyanide from sodium nitroprusside (see, for example, Vessy and Cole, in Br. J. Anaesth. 57:148–155 (1985)) and laetrile (see, for example, Sadoff et al., in J. Am. Med. Assoc. 239:1532 (1978)) can create a life-threatening situation.

Acute cyanide poisoning of mammals is characterized by convulsion, uncoordinated movement, decreased motor activity, coma and respiratory arrest, symptoms indicating that the brain is one major target site for cyanide. This type of neurotoxicity is now known to be caused by cyanide-induced depletion of dopamine (see, for example, Kanthasamy et al., in Toxicol. App. Pharmacol. 126:156–163 (1994)) and by an increase in calcium in the brain (see, for example, Yamamoto, in Toxicol. 61:221–228 (1990)). The systemic toxic effect of cyanide has been attributed mainly to its binding to the ferric iron in cytochrome c oxidase, the terminal oxidase enzyme of the mitochondrial respiratory chain. The reaction forms a stable but reversible complex and subsequently disrupts cellular energy production. The reduction of cellular oxygen consumption results in an increase in venous oxygen partial pressure ($PO_2$).

The classic antidotal action for cyanide poisoning, introduced by Chen et al. in 1933 (see, for example, Chen et al., Proc. Soc. Exp. Biol. Med. 31:250–252 (1933)), involves inhalation of amyl nitrite, followed by intravenous injection of sodium nitrite and sodium thiosulfate. This procedure is still used clinically worldwide, including the United States (see, for example, Dreisbach, in Handbook of poisoning: Diagnosis and treatment, 12th edn., Lange Med. Publications., Los Altos, Calif., p.251 (1987)). In essence, in this method, oxyhemoglobin in red blood cells in the circulation is converted into methemoglobin by chemical reaction with nitrites. Methemoglobin then binds cyanide, thereby removing it from the circulation. Sodium thiosulfate is used as a sulfur donor to allow the formation of thiocyanate, through the reaction catalyzed by rhodanese enzyme (see, for example, Baskin et al., in J. Clin. Pharmacol. 32:368–375 (1992)).

There are, however, major drawbacks of the nitrite/sodium thiosulfate method. For example, the rate of methemoglobin formation is quite slow, taking up to 20 minutes to produce sufficient amounts of methemoglobin. Moreover, the formation of methemoglobin compromises the oxygen-carrying capacity of red blood cells. This is particularly undesirable for victims of smoke inhalation, as adequate ventilation and blood oxygenation are particularly crucial for survival in such situations. Furthermore, hypotension induced by the treatment (i.e., nitrite-induced hypotension) can be life-threatening.

In addition to nitrites, a variety of chemical agents have been used to induce methemoglobinemia as a treatment for cyanide poisoning. These include primaquine phosphate, 6-methoxy-8-(6-diethylamino-hexylamino)lepidine dihydrochloride, p-aminooctoyl-phenone, p-aminopropiophenone, hydroxylamine, 4-dimethylaminophenol, and the like (see, for example, Scharf et al., in Gen. Pharmacol. 23:19–25 (1992)). Although the rates of methemoglobin formation induced by these agents are faster than those produced by nitrites, the same problems as described above are common to all methemoglobin formers.

Recently, hydroxocabalamin, vitamin $B_{12}$, has been shown to be effective in the treatment of cyanide poisoning in smoke inhalation (see, for example, Houeto et al., in Lancet 346:605–608 (1995)). Hydroxocabalamin is a cobalt-containing compound for which only minute amounts are needed physiologically. Clinical use of hydroxocabalamin for the treatment of cyanide poisoning, however, requires the use of 5 grams per patient. Such high levels of hydroxocabalamin are not only expensive but also potentially toxic because extremely high circulatory levels of cobalt are produced.

Nitroprusside (SNP for sodium nitroprusside) is widely used as a source of nitric oxide for the treatment of severe hypertension, induction of arterial hypotension during surgery, the reduction of after-load after myocardial infarction and during severe congestive heart failure (see, for example, Rokonen et al., in Crit. Care Med. 21:1304–1311 (1993) and Sellke et al., in Circulation 88:II395–II400 (1993)). A nitroprusside molecule ($NaFe(CN)_5NO.2H_2O$) contains one nitric oxide and five cyanide groups. Upon intravenous infusion, nitroprusside is known to be metabolized through one-electron reduction to release nitric oxide, a potent vasodilator, which exerts the desired antihypertensive effect (see, for example, Bates et al., in Biochem. Pharmacol. 42:S157–S165 (1991) and Kowaluk et al., in J. Pharm. Exp. Therap. 262:916–922 (1992)). Unfortunately, however, upon release of nitric oxide, SNP further decomposes to release five cyanide groups which can produce life-threatening cyanide poisoning in patients. This high level of cyanide release occurs very commonly in high dose or prolonged therapy with nitroprusside.

Current clinical treatment of nitroprusside-induced cyanide toxicity is, unfortunately, limited to the use of amyl nitrite and sodium nitrite (for the conversion of hemoglobin to methemoglobin) or vitamin $B_2$. The many drawbacks of using these agents have been set forth above.

Another chemical species whose effect can be detrimental when levels arise above physiological levels is iron. Iron is crucial for maintaining normal structure and function of virtually all mammalian cells (see, for example, Voest et al., in *Ann. Intern. Med.* 120:490–499 (1994) and Kontoghiorghes, G. J., in *Toxicol. Letters* 80:1–18 (1995)). Adult humans contain 3–5 g of iron, mainly in the form of hemoglobin (58%), ferritin/hemosiderin (30%), myoglobin (9%) and other heme or nonheme enzyme proteins (Harrison and Hoare, in *Metals in Biochemistry*, Chapman and Hall, New York, 1980).

Total iron levels in the body are regulated mainly through absorption from the intestine and the erythropoietic activity of the bone marrow. Upon absorption, iron is transported to various tissues and organs by the serum protein transferrin. Once transported to the target tissue or organ, iron is transported and stored intracellularly in the form of ferritin/hemosiderin. Under normal conditions, transferrin is about 30% saturated with iron in healthy individuals, and an equilibrium is maintained between the sites of iron absorption, storage and utilization. The presence of these homeostatic controls ensures the maintenance of physiological levels of not only iron, but also other essential metal ions such as copper, zinc and cobalt.

Breakdown of these controls could result in metal imbalance and metal overload, causing iron overloading toxicity and possibly death in many groups of patients, especially those with idiopathic hemochromatosis (see, for example, Guyader et al., in *Gastroenterol.* 97:737–743 (1989)). Among its toxic effects, iron is known to mediate a repertoire of oxygen related free radical reactions (see, for example, Halliwell and Gutteridge, in Halliwell and Gutteridge, Free Radicals in Biology and Medicine, 2nd edition. Oxford: Clarendon Press, 15–19 (1989)). For example, iron, particularly in the form of free iron ions, can promote the generation of reactive oxygen species through the iron-catalyzed Haber-Weiss reaction (see, for example, Haber and Weiss, in *Proc. R. Soc. Ser. A.* 147:332 (1934)) as follows:

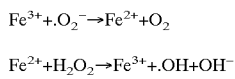

$$Fe^{3+} + .O_2^- \rightarrow Fe^{2+} + O_2$$

$$Fe^{2+} + H_2O_2 \rightarrow Fe^{3+} + .OH + OH^-$$

The net result of these reactions is as follows:

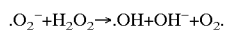

$$.O_2^- + H_2O_2 \rightarrow .OH + OH^- + O_2.$$

The Haber-Weiss reaction is seen to produce the hydroxyl radical (.OH), a highly potent oxidant which is capable of causing oxidative damage to lipids, proteins and nucleic acids (see, for example, Lai and Piette, in *Biochem. Biophys. Res. Commun.* 78:51–59 (1977); and Dizdaroglu and Bergtold, in *Anal. Biochem.*, 156:182 (1986)).

The occurrence of iron imbalance resulting in excessive in vivo iron levels can be categorized into two conditions, namely iron-overload and non-iron overload conditions (see, for example, Voest et al., supra; Kontoghiorghes, supra). Iron-overload conditions are common in such patients as those suffering from thalassemia, sickle cell anemia, repeated blood transfusion and hereditary hemochromatosis. In such patients, transferrin is fully saturated with iron, and excess low-molecular-weight iron appears in the serum. This low-molecular-weight iron appears to originate from the iron released mainly from the liver and spleen, and from the breakdown of effete red cells. Other iron overload diseases and conditions include hereditary spherocytosis, hemodialysis, dietary or latrogenic iron intake, intramuscular iron dextran and hemolytic disease of the newborn (see, for example, Voest et al., supra; Kontoghiorghes, supra).

Non-iron overload conditions relate to situations where elevated iron levels are the result of therapeutic intervention, such as, for example, anthracycline anti-cancer therapy or inflammatory diseases such as rheumatoid arthritis. While anthracyclines such as adriamycin (doxorubicin) are effective in the treatment of a number of neoplastic diseases, these compounds have limited clinical utility due to the high incidence of cardiomyopathy (see, for example, Singal et al., in *J. Mol. Cell. Cardiol.* 19:817–828 (1987)).

The molecular mechanism of cardiomyopathy is now attributed to the adriamycin-induced release of iron from intracellular iron-containing proteins, resulting in the formation of an adriamycin-iron complex, which generates reactive oxygen species causing the scission and condensation of DNA, peroxidation of phospholipid membranes, depletion of cellular reducing equivalents, interference with mitochondrial respiration, and disruption of cell calcium homeostasis (see, for example, Myers et al., *Science* 197:165–167 (1977); and Gianni et al., in *Rev. Biochem. Toxicol.* 5:1—82 (1983)). On the other hand, several clinical studies have shown that patients with rheumatoid arthritis exhibit elevated low-molecular weight iron species and ferritin-bound iron levels in synovial fluid. Iron, presumably via its mediation of oxygen free radical pathways, exerts its proinflammatory effects in rheumatoid arthritis (see, for example, Muirden and Senator, in *Ann. Rheum. Dis.* 27:38–48 (1968); and Biemond et al., in *Arthritis Rheum.* 29:1187–1193 (1986)).

Iron also plays an important role in many aspects of immune and nonimmune host response (see, for example, De Sousa et al., in *Ann. N.Y. Acad Sci.* 526:310–323 (1988)). It is known that increased concentrations of iron are deleterious to the immune system through the initiation or maintenance of inflammatory reactions (see, for example, Biemond et al., in *J. Clin. Invest.* 73:1576–9 (1984), and Rowley et al., in *Clin. Sci.* 66:691–5 (1984)). Other non-iron overload diseases and conditions include reperfusion injury, solid tumors (e.g., neuroblastoma), hematologic cancers (e.g., acute myeloid leukemia), malaria, renal failure, Alzheimer's disease, Parkinson's disease, inflammation, heart disease, AIDS, liver disease (e.g., chronic hepatitis C), microbial/parasitic infections, myelofibrosis, drug-induced lung injury (e.g., paraquat), graft-versus-host disease and transplant rejection and preservation.

Hence, not surprisingly, there has been a tremendous interest in the therapeutic use of chelators in the treatment of both iron-overload and non-iron overload diseases and conditions. A chelator (Greek, chele-claw of a crab) is a molecule forming a cyclic ring with a metal as the closing member. Hundreds of chelating agents have been designed and developed for animal and human studies. Among them, at least fifteen different chelators have been used in humans, including desferrioxamine (DF), ethylenediaminetetraacetic acid (EDTA), diethylenetriamine pentaacetic acid (DTPA), pyridoxalisonicotinoylhydrazone (PIH), 1,2-dimethyl-3-hydroxypyrid-4-one (L1) and [+]1,2-bis-(3,5-dioxopiperazine-1-yl) propane (ICRF-187).

For the past 30 years, DF (i.e., desferrioxamine) has been the most commonly used chelating drug for the treatment of transfusional iron overload (see, for example, Pippard et al., in *Blood* 60:288–294 (1982); Proper et al., in *N. Engl. J. Med.* 294:1421–1423 (1976); and St. Louis et al., in Lancet 336:1275–1279 (1990)). Patients suffering from thalassemia lived longer with the DF treatment. However, major drawbacks in the use of DF include the cost thereof (~$7,000/patient/year), which can be affordable only by a very small percentage of thalassemia patients worldwide. Another drawback to the use of DF includes the toxicity thereof, including ophthalmic and auditory toxicities as well as induction of pulmonary and renal damage.

Unlike DF, L1 (i.e., 1,2-dimethyl-3-hydroxypyrid-4-one) and related compounds are orally available iron chelators, showing promise in improving the quality of life in patients with thalassemia (see, for example, Olivieri et al., in *Drugs Today* 28(Suppl. A):123–132 (1992)) and rheumatoid arthritis (see, for example, Vreugdenhil et al., in *Lancet* 2:1398–9 (1989)). However, the major side effects of L1 therapy include myclosuppression, fatigue, and maternal, embryo and teratogenic toxicity, which severely limits the potential clinical applications thereof (see, for example, Kontoghiorghes, in *Int. J. Hematol.* 55:27–38 (1992)).

Recently, ICRF-187 has been demonstrated to be effective in removing iron from the anthracycline-iron complex, therefore preventing the cardiac toxicity in cancer patients receiving adriamycin chemotherapy (see, for example, Kolaric et al., in *Oncology* 52:251–5 (1995)). However, when chelated with iron, the iron-ICRF-187 complex per se is also very effective in the promotion of hydroxyl radical generation via the Fenton reaction, causing oxidative damage to tissues (see, for example, Thomas et al., in *Biochem. Pharmacol.* 45:1967–72 (1993)). In addition, since ICRF-187 is a strong chelator (having a structure similar to EDTA), it chelates not only low-molecular-weight iron, but also chelates iron from transferrin and ferritin, as well as copper from ceruloplasmin, thus potentially affecting normal cellular iron metabolism.

Another major complication in the therapeutic use of chelators is the propensity of chelators to affect not only the desired metal but also many other essential metals, their associated metabolic pathways and other processes. Thus, for example, the treatment with DF and L1 requires zinc supplementation to prevent the occurrence of zinc deficiency diseases (see, for example, De Virgilis et al., Arch. Dis. Chil. 63:350–255 (1988); and Al-Refai et al., Blood 80:593–599 (1992)).

The low-molecular-weight iron pool in serum is thought to be the most labile iron source during chelation therapy. Chelators that remove this low molecular weight iron with only a minimal effect on other essential metal contents in the body are highly desirable, particularly for the treatment of transfusion-induced iron overload, as well as iron overload induced by anthracycline anti-cancer agents, inflammatory diseases such as rheumatoid arthritis, multiple sclerosis, and the like.

Chronic exposure of the skin to sunlight or ultraviolet radiation can cause severe damage to the underlying connective tissue, leading to erythema and other skin diseases (see, for example, Beisset and Granstein in Crit. Rev. Biochem. Mol. Biol. 31:381–404 (1995) and Kaminester in Arch. Fam. Med. 5:289 (1996). Although the mechanism by which photodamage occurs is not well understood, reactive oxygen species (such as singlet oxygen, superoxide and hydrogen peroxide) and reactive nitrogen species (such as nitric oxide and peroxynitrite) have been implicated as important contributors to such damage (see, for example, Jurkiewicz and Buettner in Photochem. Photobiol. 59:1–4 (1994), Deliconstantinos et al., in Biochem. Pharmacol. 51:1727–1738 (1996) and Deliconstantinos et al., in Brit. J. Pharmacol. 114:1257–1265 (1995)). The skin is known to contain high levels of iron (see, for example, Bissett et al., in Photochem. Photobiol. 54:215–223 (1991). Upon release intracellularly by ultraviolet radiation, iron can participate in oxygen radical formation, thus enhancing the likelihood of causing photodamage, and enhancing the level of photodamage which actually occurs. For example, the combination topical application of the iron chelator, 2-furildioxime, in combination with sunscreen, has been shown to produce synergistic photoprotection (see, for example, Bissett et al., in J. Am. Acad. Dermatol. 35:546–549 (1991)). However, further development in the field is needed to produce more effective and safer iron chelators for the prevention of photoaging and photodamage.

Since a variety of stimuli induce expression of nitric oxide synthase, which, in turn, leads to nitric oxide overproduction (with its attendant detrimental effects), there is a need in the art to effectively treat both the initial stimulus of nitric oxide synthase expression, and the resulting overproduction of nitric oxide, as well as overproduction of nitric oxide which may be induced (directly or indirectly) by therapeutic agents employed for the treatment of a wide variety of infectious and/or inflammatory conditions. There is also still a need in the art for effective, rapid acting, non-toxic antidotes for cyanide poisoning and for new iron scavengers that are capable of removing free iron ions from body fluids, without affecting the normal cellular iron metabolism.

BRIEF DESCRIPTION OF THE INVENTION

In accordance with one aspect of the present invention, methods have been developed for the in vivo reduction of levels of nitric oxide, such as are induced by a variety of disease states. In accordance with another aspect of the present invention, combinational therapeutic methods have been developed for the in vivo inactivation or inhibition of formation (either directly or indirectly) of species which induce the expression of inducible nitric oxide synthase, as well as reducing nitric oxide levels produced as a result of .NO synthase expression. In another aspect, combinational therapeutic methods have been developed which can be employed, for example, for the treatment of infectious and/or inflammatory conditions. Thus, the effectiveness of many therapeutic agents used for the treatment of infectious and/or inflammatory conditions can be enhanced by co-administration thereof in combination with disulfide derivatives of dithiocarbamate(s) that, when activated, are effective as nitric oxide scavenger(s).

In one aspect, the present invention relates to reducing elevated nitric oxide levels associated with infectious and/or inflammatory conditions (and the treatment thereof). In accordance with this aspect of the invention, a disulfide derivative of a dithiocarbamate is a administered either alone or in combination with an agent for the treatment of the infectious and/or inflammatory condition.

In another aspect, the present invention employs a combination of inactivation (and/or inhibition) and scavenging approach whereby the stimulus of nitric oxide synthase expression is inactivated and/or expression thereof is inhibited, and overproduced nitric oxide is bound in vivo to a suitable nitric oxide scavenger. The resulting complexes render the stimulus of nitric oxide synthase expression inactive (or inhibit the production thereof), while also rendering the resulting nitric oxide harmless. The resulting complexes are eventually excreted in the urine of the host.

In another aspect, a suitable nitric oxide scavenger is co-administered along with a therapeutic agent which may promote nitric oxide formation, thereby providing a protective affect against the otherwise detrimental effects of nitric oxide overproduction.

In another aspect of the invention, methods have been developed for the in vivo reduction of cyanide levels. The present invention describes the in vivo use of disulfide derivatives of dithiocarbamates that react rapidly with cyanide, thereby preventing its toxic effects. Dithiocarbamates are a class of low molecular-weight sulphur-containing compounds that are effective chelators (see, for example, Shinobu et al., Acta Pharmacol et Toxicol. 54:189–194 (1984)). For example, diethyldithiocarbamate (DETC) is used clinically for the treatment of nickel poisoning.

In contrast to the approaches described in the prior art (see references cited above), the present invention employs a scavenging approach whereby cyanide reacts in vivo with a suitable disulfide derivative of dithiocarbamate. The resulting by-products render the cyanide harmless, and are eventually excreted in the urine of the host. Further in accordance with the present invention, there have been developed compositions and formulations useful for carrying out the above-described methods.

In accordance with another aspect of the invention, methods have been developed for the in vivo reduction of free iron ion levels in a subject. The present invention employs a scavenging approach whereby free iron ions are bound in vivo to a suitable physiologically compatible disulfide derivative of a dithiocarbamate, which, when activated, is effective as an iron scavenger, i.e., a compound capable of binding free iron ions. The resulting complex renders the free iron ions harmless, and is eventually excreted in the urine of the host.

Further in accordance with the present invention, there have been developed compositions and formulations useful for carrying out the above-described methods.

It is known that endotoxin challenge induces the release of cellular iron from tissues (see, for example, Kim et al., in *J. Biol. Chem.* 270:5710–5713 (1995)). Thus, the invention method(s) removes free iron in vivo, particularly during the infectious and inflammatory conditions where intracellular iron loss is common, therefore preventing iron-induced oxidative damage to the tissues.

Further, in accordance with the present invention, there have been developed compositions and formulations containing a disulfide derivative of a dithiocarbamate for carrying out the above described methods.

DETAILED DESCRIPTION OF THE INVENTION

Figure 1:
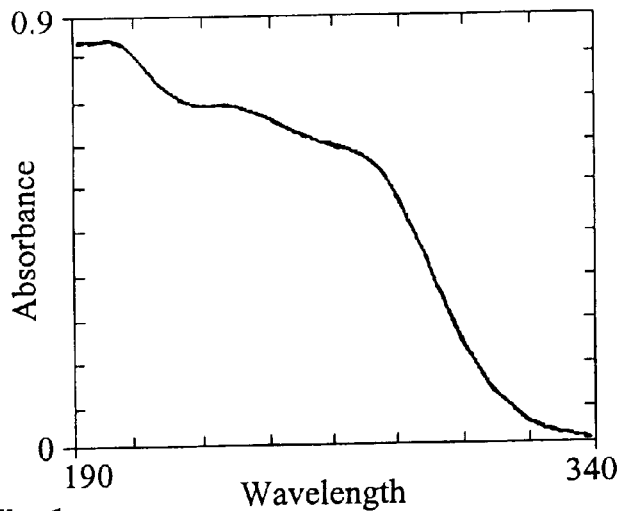
FIG. 1 is an illustration of the UV spectrum of N-methyl-D-glucamine dithiocarbamate disulfide (MGDD) in water (final concentration 10 $\mu$g/ml. The spectrum was recorded using a Hewlett-Packard Diode Array Spectrophotometer, with a scanning wavelength of 190 nm to 340 nm, at room temperature.

In accordance with the present invention, there are provided therapeutic methods for treating a variety of conditions related to the overproduction of nitric oxide by a subject and the presence of elevated levels of nitric oxide in a subject as a result of such overproduction. In one aspect, the invention method comprises administering to a subject in need thereof an effective amount of a disulfide derivative of a dithiocarbamate, which, when activated, is effective as a nitric oxide scavenger.

Nitric oxide overproduction is associated with a wide range of disease states and/or indications. such as, for example, septic shock, ischemia, administration of cytokines, overexpression of cytokines, ulcers, inflammatory bowel disease (e.g., gastritis, ulcerative colitis or Crohn's disease), diabetes, arthritis (e.g., rheumatoid arthritis), asthma, Alzheimer's disease, Parkinson's disease, multiple sclerosis, cirrhosis, allograft rejection (e.g., transplant rejection), encephalomyelitis, meningitis, pancreatitis, peritonitis, vasculitis, lymphocytic choriomeningitis, glomerulonephritis, ophthalmologic diseases (e.g., uveitis, glaucoma, blepharitis, chalazion, allergic eye disease, corneal ulcer, keratitis, cataract, retinal disorders, age-related macular degeneration, optic neuritis, and the like), ileitis, inflammation induced by overproduction of inflammatory cytokines (e.g., liver inflammation, renal inflammation, airway inflammation, and the like), hemorrhagic shock, anaphylactic shock, burn, infection leading to the overproduction of inflammatory cytokines (including bacterial (e.g., *E. coli* infection), viral (e.g., HIV), fungal (e.g., Candidiosis and histoplasmosis) and parasitic (e.g., Leishmaniasis and Schistosomiasis) infections), hemodialysis, chronic fatigue syndrome, stroke, cancers (e.g., breast, melanoma, carcinoma, and the like), cardiovascular diseases associated with overproduction of inflammatory cytokines (e.g., heart disease, cardiopulmonary bypass, ischemic/reperfusion injury, and the like), ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, neurodegenerative disorders (e.g., chronic neurodegenerative disease), chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), transplant rejection and preservation, fertility enhancement, bacterial translocation, circulatory shock, traumatic shock, and the like. In another aspect, the invention methods comprise directly or indirectly treating the production of species which induce the expression of inducible nitric oxide synthase in a subject by co-administering to a subject an effective amount of a combination of at least one agent capable of directly or indirectly inactivating said species, or inhibiting production of said species, and at least one disulfide derivative of a dithiocarbamate, which, when activated, is effective as a nitric oxide scavenger.

Presently preferred indications for treatment in accordance with the present invention include septic shock, ischemia, administration of IL-1, administration of IL-2, administration of IL-6, administration of IL-12, administration of tumor necrosis factor, administration of interferon-gamma, ulcers, ulcerative colitis, diabetes, arthritis, asthma, Alzheimer's disease, Parkinson's disease, multiple sclerosis, cirrhosis or allograft rejection. Especially preferred indications for treatment in accordance with the present invention include nitric oxide overproduction associated with septic shock and nitric oxide overproduction associated with cytokine therapy.

The present invention also relates to combinational therapeutic methods for treating the production of species which induce the expression of nitric oxide synthase in mammals. Thus, a dual attack is mounted against a variety of stimuli which lead to the production of dangerously high in vivo levels of .NO. Combinations of agents contemplated for use in the practice of the present invention (i.e., agents capable of inactivating species which induce expression of inducible nitric oxide, or agents which inhibit the production of such species, or therapeutically useful agents which also induce nitric oxide production, and invention compositions) are administered to a host in need of such treatment. The agent capable of inactivating (or inhibiting the production of) species which induce expression of inducible nitric oxide and the active species released from the invention disulfide derivatives of dithiocarbamates interact with the stimulus or stimuli of nitric oxide synthase expression and in vivo produced .NO, respectively, forming a complex between said species and said agent, as well as a stable scavenger-NO complex (e.g., a dithiocarbamate-metal-NO complex). Whereas free .NO is a potent vasodilator, chelated .NO complexes (e.g., .NO chelated with dithiocarbamate-iron complexes) are not. The NO-containing complex is then filtered through the kidneys, concentrated in the urine, and eventually excreted by the subject, thereby reducing in vivo .NO levels.

In accordance with another aspect of the present invention therefore, combinational therapeutic methods have been developed employing an effective amount of a combination of at least one treating agent useful for the treatment of infectious and/or inflammatory conditions, and at least one dithiocarbamate-containing nitric oxide scavenger according to the invention. It has been found that the above-described combination is more effective for the treatment of infectious and/or inflammatory conditions than is the treating agent alone.

In accordance with another aspect of the present invention, there are provided therapeutic compositions comprising a pharmaceutically or cosmetically acceptable carrier and a disulfide derivative of a dithiocarbamate having a generic structure (I) as follows:

$$R_1R_2N\text{—}C(S)\text{—}S\text{—}S\text{—}(S)C\text{—}NR_2R_1 \qquad (I)$$

wherein:
each $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or $R_1$ and $R_2$ can cooperate to form a 5-, 6- or 7-membered ring including N, $R_1$ and $R_2$, or $R_1$ or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species, except for disulfide derivatives of diethyldithiocarbamate, di-pentamethylen-thiuramdisulfide, and di-pentamethylen-thiuramdisulfide.

Presently preferred compounds having the above-described generic structure (I) are those wherein:
each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl.

Especially preferred compounds having the above-described generic structure are those wherein:
$R_1$=a $C_2$ up to $C_8$ alkyl or substituted alkyl, wherein the substituents are selected from carboxyl, acetyl, pyridinyl, pyrrolidinyl, amino, amido, hydroxy or nitro, and $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$ The presently most preferred compounds having the above-described generic structure are those wherein:

$R_1$=a $C_2$ up to $C_8$ alkyl or substituted alkyl, wherein the substituents are selected from carboxyl, acetyl, amido or hydroxy, and $R_2$=a $C_1$ up to $C_4$ alkyl or substituted alkyl.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkylene, alkenylene or —O—, —S—,—C(0)— and/or —N(R)— containing alkylene moieties, wherein R is hydrogen or a lower alkyl moiety.

As employed herein, "substituted alkyl" comprises alkyl groups further bearing one or more substituents selected from hydroxy, alkoxy (of a lower alkyl group; wherein a lower alkyl group has about 1–4 carbon atoms), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkyl-carbonyl species.

As employed herein, "halogen" refers to fluoride, chloride, bromide or iodide atoms.

The invention disulfide derivatives of dithiocarbamates are particularly well suited for oral or local administration because they are stable at the pH in the stomach (and have been shown to be stable at pH 1 for up to 24 hours) but release the active monomers under slightly reducing conditions, such as are found in the lower alimentary tract, in skin and in tissue.

Accordingly, there are provided pharmaceutical compositions comprising a pharmaceutically acceptable carrier, a dithiocarbamate derivative having structure I, and optionally further including a simple reducing agent, such as L-cysteine or glutathione, and the like, in an amount sufficient to reduce the disulfide bond in the disulfide derivative.

In another aspect, a method is provided for inhibiting nuclear factor kappa B (NFκB) pathways by administering to a subject in need thereof an effective amount of one or more of the invention disulfide derivatives of dithiocarbamates, such as the disulfide derivative of pyrrolidine dithiocarbamate. Pyrrolidine dithiocarbamate, although shown effective for inhibiting NFκB pathways, breaks down to ineffective species in the presence of stomach acid. However, the invention disulfide derivative of pyrrolidine dithiocarbamate, being stable at pH 1 for as long as 24 hours, can be administered orally and will release the active dithiocarbamate species in the reducing conditions of the lower alimenary tract. Alternatively, the disulfide derivative can be administered locally and will release the active species due to the reducing conditions in the skin or tissue, thereby avoiding the toxicity risk inherent in systemic administration of the compound.

As readily understood by those of skill in the art, a wide variety of agents and/or conditions induce expression of inducible nitric oxide synthase, e.g., cytokines. cytokine receptors, endotoxins, platelet activating factors, bradykinins, bradykinin receptors, bacteria, parasites, viruses, coagulation factors, arachidonate metabolites, nitric oxide synthase, nuclear factor kappa B, ultraviolet light, gamma ray irradiation, elevated temperature, oxygen radicals, and the like.

Induction of expression of inducible nitric oxide synthase, and hence, overproduction of nitric oxide, is associated with a wide range of disease states and/or indications, such as, for example, septic shock, hemorrhagic shock, anaphylactic shock, toxic shock syndrome, ischemia, cerebral ischemia, administration of cytokines, overexpression of cytokines, ulcers, inflammatory bowel disease (e.g., gastritis, ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, ophthalmologic diseases (e.g., uveitis, glaucoma, blepharitis, chalazion, allergic eye disease, corneal ulcer, keratitis, cataract, retinal disorders, age-related macular degeneration, optic neuritis, and the like), ileitis, inflammation (e.g., liver inflammation, renal inflammation, airway inflammation, and the like), burn, infection (including bacterial (e.g., *E. coli* infection), viral (e.g., HIV), fungal (e.g., Candidiosis and histoplasmosis) and parasitic (e.g., Leishmaniasis and Schistosomiasis) infections), hemodialysis, chronic fatigue syndrome, stroke, cancers (e.g., breast, melanoma, carcinoma, and the like), cardiovascular diseases associated with overproduction of inflammatory cytokines (e.g., heart disease, cardiopulmonary bypass, ischemic/reperfusion injury, and the like), ischemic/reperfusion associated with overproduction of inflammatory cytokines, adult respiratory distress syndrome, cachexia, myocarditis, autoimmune disorders, eczema, psoriasis, heart failure, atherosclerosis, dermatitis, urticaria, systemic lupus erythematosis, AIDS, AIDS dementia, neurodegenerative disorders (e.g., chronic neurodegenerative disease), chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), myasthenia gravis (MG), transplant rejection and preservation, fertility enhancement, bacterial translocation, circulatory shock, traumatic shock, alcohol hang-over, and the like.

Treatment of such conditions can be carried out with a variety of reagents, such as, for example, inhibitors of cytokine synthesis/release (e.g., anti-cytokine antibodies, anti-cytokine receptor antibodies, and the like), anti-endotoxin antibodies, bradykinin antagonists, synthetic peptide blocking bradykinin receptors, bactericidal/permeability increasing protein, inhibitors of the coagulation cascade (e.g., antibodies to platelet activating factor), inhibitors of complement activation, inhibitors of arachidonate metabolism, inhibitors of nitric oxide synthase enzymes, immunosuppressors, diabetic therapeutic agents, anti-inflammatories, agents useful for stroke therapy, agents useful for asthma therapy, agents useful for cirrhosis therapy, anti-cancer therapeutics, anti-microbial therapeutics, anti-fungal therapeutics, anti-retroviral therapeutics, agents useful for the treatment of opportunistic infections and malignancies, agents useful for the treatment of Lupus erythmatosus, agents useful for the treatment of uveitis, thrombolytic agents, antispasmodic agents, antidiarrheal agents, agents useful for the treatment of constipation, antihistamines, agents useful for the treatment of Parkinson's disease, therapeutic agents for Crohn's disease therapy, anti-oxidants, and the like.

The invention disulfide derivatives of dithiocarbamates, which, when activated, are effective as nitric oxide scavengers, either alone or in combination with such agents, can be used for a variety of indications, such as for example, anti-endotoxin therapy (e.g., antibodies to endotoxin, antibodies to LPS-binding protein, soluble CD14 protein, bactericidal/permeability increasing protein, polymyxin B, and the like), inhibition of cytokine synthesis/release (e.g., employing phosphodiesterase inhibitors, IL-4, IL-10, IL-13, TGF-β, corticosteroids, and the like), anti-cytokine therapy (e.g., employing antibodies to TNF, soluble TNF receptors, IL-1 receptor antagonists, antibodies to IL-1 receptors, antibodies to IL-6, antibodies to interferon-γ, soluble interferon-γ receptors, and the like), inhibition of the coagulation cascade (and of complement activation, employing such agents as anti-Factor XII antibodies, antibodies to C5a, C1-esterase inhibitors, soluble Cr1, and the like), inhibition of platelet activating factor (PAF, employing such agents as PAF receptor antagonists, and the like), inhibition of arachidonate metabolism (e.g., employing agents such as cyclooxygenase inhibitors, lipoxygenase inhibitors, leukotriene inhibitors, thromboxane $A_2$ inhibitors, prostaglandins, and the like), inhibition of nitric oxide synthase enzymes (e.g., employing arginine analogs (such as L-$N^G$-methylarginine, L-$N^G$-nitroarginine, L-$N^G$-aminoarginine, L-iminoethylornithine, ε-N-iminoethyl-L-lysine, L-$N^G$-nitroarginine methyl ester, L-$N^G$-hydroxyl-$N^G$-methylarginine, L-$N^G$-methyl-$N^G$-methylarginine, L-thiocitrulline, L-S-methylthiocitrulline, L-S-ethylisothiocitrulline, S-ethylisothiocitrulline, aminoguanidine, S-methyl isothiourea sulfate, and the like), heme ligands (such as 7-nitroindazole, 7,7,8,8-tetramethyl-o-quinodimethane, imidazole, 1-phenylimidazole, 2-phenylimidazole, and the like), calmodulin antagonists (such as chlorpromazine, W-7, and the like), and the like);

immunosuppression (e.g., employing one or more agents such as cyclosporin A, OKT3, FK506, mycophenolate mofetil (MMF), azathioprine, corticosteroids (such as prednisone), antilymphocyte globulin, antithymocyte globulin, and the like), diabetic therapy (e.g., employing one or more agents such as free pancreatic islets, encapsulated pancreatic islets, oral insulin, intravenous insulin, amylin hormone, and the like), dihydropyridine calcium channel blockers (e.g., employing agents such as nifedipine, nitrendipine, nisoldipine, and the like), acetohexamide, chlorpropamide, glyburide, glipizide, metformin, tolbutamide, tolazamide, and the like, inflammatory disease therapy (e.g., employing disease-modifying agents (such as antimalarials, methotrexate, sulfasalazine, mesalamine, azathioprine, 6-mercaptopurine, metronidazole, injectable and oral gold, D-penicillamine, and the like), corticosteroids, non-steroidal antiinflammatory drugs (such as acetominophen, aspirin, sodium salicylate, magnesium salicylate, choline magnesium salicylate, salicylsalicylic acid, ibuprofen, naproxen, diclofenac, diflunisal, etodolac, fenoprofen calcium, fluriprofen, piroxicam, indomethacin, ketoprofen, ketorolac tromethamine, meclofenamate, meclofenamate sodium, mefenamic acid, nabumetone, oxaprozin, phenyl butyl nitrone (PBN), sulindac, tolmetin, and the like), and the like), stroke therapy (e.g., employing one or more agents such as fibrinolytic agents (such as streptokinase, acylated plasminogenstreptokinase complex, urokinase, tissue plasminogen activator, and the like), employing monoclonal antibodies directed against leukocyte adhesion molecules (such as intercellular adhesion molecule-1 (ICAM-1), CD18, and the like), hemodilution therapy (employing modified hemoglobin solutions such as diaspirin crosslinked hemoglobin), employing growth factors (such as basic fibroblast growth factor (bFGF), transforming growth factor-beta 1 (TGF-β1), and the like), employing glutamate antagonists (such as lamotrigine, dizolcilpine maleate (MK 801), BW619C89, BW1003C87, and the like), employing NMDA antagonists (such as CGS 19755 (Selfotel), aptiganel hydrochloride, dextrorphar, d-CPPene, and the like), employing GABA agonists (such as muscimol), employing free radical scavengers (such as allopurinol, S-PBN, 21-aminosteroids, tocopherol, superoxide dismutase, dexanabinol (HU-211), selenium, carotenoids, and the like), idebenone, ticlopidine, lovastatin, citicoline, and the like), asthma therapy (e.g., employing bronchodilators (such as albuterol, salmeterol, metaproternol, bitolterol, pirbuterol, terbutaline, isoproterenol, epinephrine, and the like), theophyllines (such as theophylline, aminophylline, and the like), corticosteroids (such as beclomethasone, prednisone, and the like), antimediators (such as cromolyn sodium, nedocromil sodium, and the like), and the like), cirrhosis therapy (e.g., employing diuretics (such as spironolactone), opiate antagonists (such as naloxone), cholestyramine, colchicine, colestipol, methotrexate, rifampin, ursodeoxycholic acid, and the like, anti-cancer therapy (e.g., employing one or more agents such as alkylating agents (such as mechlorethamine, chlorambuccil, ifosfamide, melphalan, busulfan, carmustine, lomustine, procarbazine, dacarbazine, cisplatin, carboplatin, and the like), antimetabolites (such as methotrexate, mercaptopurine, thioguanine fluorouracil, cytarabine, and the like), hormonal agents (such as testosterone propionate, fluoxymesterone, flutamide, diethylstilbestrol, ethinyl estradiol, tamoxifen, hydroxyprogesterone caproate, medroxyprogesterone, megestrol acetate, and the like), adrenocorticosteroids (such as prednisone), aromatase inhibitors (such as amino glutethimide), leuprolide, goserelin acetate, biological response modifiers (such as interferon-α2a, interferon-α2b, interleukin-2, and the like), peptide hormone inhibitors (such as octreotide acetate), natural products (such as vinblastine, vincristine, vinorelbine, paclitaxel, dactinomycin, daunorubicin, idarubicin, doxorubicin, etoposide, plicamycin, mitomycin, mitoxantrone, bleomycin, hydroxyurea, mitotane, fludarabine, cladribine, and the like), supportive agents (such as allopurinol, mesna, leucovorin, erythropoietin, filgrastim, sargramostim, and the like), and the like, anti-microbial therapy (e.g., employing one or more agents such as celftriaxone, TMP-SMZ, penicillin, aminoglycosides, vancomycin, gentamicin, rifampin, imipenem, clindamycin, metronidazole, tetracycline, erythromycin, sulfonamide, streptomycin, ampicillin, isoniazid, pyrazinamide, ethambutol, and the like), anti-fungal therapy (e.g., employing agents such as amphotericin B, griseofulvin, myastatin, flucytosine, natamycin, antifungal imidazoles (e.g., clotrimazole, miconazole, ketoconazole, fluconazole, itraconazole, and the like), and the like, anti-retroviral therapy (e.g., employing agents such as protease inhibitors (such as Invirase, Ritonavir, Crixivan, and the like), zidovudine, didanosine, zalcitabine, stavudine, viramune, and the like)

treatment of opportunistic infections and malignancies (e.g., anti-AIDS treatment, employing agents such as pentamidine, trimethoprim/sulfamethoxazole, primaquine, atovaquone, clarithromycin, clofazimine, ethambutol, rifampin, amikacin, ciprofloxacin, pyrimethamine, amphotericin B, ganciclovir, foscarnet, fluconazole, ketoconazole, acyclovir, and the like), Lupus erythymatosus therapy (e.g., employing agents such as hydroxychloroquine sulfate, chloroquine sulfate, quinacrine, dapsone, isotretinoin, and the like), uveitis therapy (e.g., employing agents such as corticosteroids, azathioprine, cyclosporine, and the like), thrombolytic therapy for acute myocardial infarction (e.g., employing agents such as streptokinase, tissue plasminogen activator (t-PA), anistreplase, and the like), antispasmodic treatment (e.g., employing agents such as dicyclomine, hyoscyamine, propantheline, and the like), antidiarrheal treatment (e.g., employing agents such as loperamide, diphenoxylate with atropine, and the like), anticonstipation treatment (e.g., employing agents such as fiber supplementation with bran, psyllium, methylcellulose, polycarbophil, cisapride, and the like), antihistamine therapy (e.g., employing agents such as ethanolamines (such as diphenhydramine, clemastine, and the like), ethylenediamines (such as brompheniramine, chlorpheniramine, triprolidine, and the like), phenothiazines (such as hydroxyzine), piperidines (such as terfenadine, astemizole, azatadine. cyproheptadiene, loratidine, and the like), and the like), anti-Parkinsonian therapy (e.g., employing agents such as benztropine mesylate, biperiden, chlorphenoxamine, cycrimine, orphenadrine, procyclidine, trihexyphenidyl, and the like), as well as other indications which involve the induction of nitric oxide synthase, as can readily be identified by those of skill in the art.

In addition, co-administration of therapeutic agents suitable for treatment of a wide variety of diseases and conditions, in combination with the invention dithiocarbamate-containing composition(s), is contemplated by the present invention. For example, the invention dithiocarbamate-containing composition(s), which, when activated, are advantageously effective as nitric oxide scavenger(s) in conjunction with the administration of immunosuppressants, such as glucocorticoids (methylprednisolone), myelin basic protein (e.g., 7-capaxone), anti-Fc receptor monoclonal antibodies, hydroorotate dehydrogenase inhibitor, anti-IL2 monoclonal antibodies (e.g., dacliximab), buspirone, castanospermine, CD-59 (complement factor inhibitor), 5-lipoxygenase inhibitor, phosphatidic acid synthesis antagonists, ebselen, edelfosine, enlimomab, galaptin, platelet activating factor antagonists, selectin antagonists, interleukin-10 agonist, macrocylic lactone, methoxatone, mizoribine, protein kinase C inhibitors, phosphodiesterase IV inhibitor, sialophorin, sirolimus, spirocyclic lactams, 5-hydroxytryptamine antagonist, and the like.

Additional treatments for which the invention dithiocarbamate-containing composition(s), which, when activated, are effective as nitric oxide scavenger(s) are advantageously employed in conjunction with the primary treating agent include administration of antimetabolite cytotoxics (e.g., azathioprine, cyclophosphamide), C5a release inhibitor, benzydamine, peldesine, pentostatin, thalidomide, benzoporphyrin derivatives, arachidonate antagonists (e.g., halometasone, halobetasol propionate), corticosteriod (clobetasol propionate), growth hormone antagonists (octapeptide somatostatin analogue, lanreotide, angiopeptin and dermopeptin), thymopentin, and the like.

Other treatments for which the invention disulfide derivatives of dithiocarbamates, which, when activated are effective as nitric oxide scavenger(s) are advantageously employed in conjunction with the primary treating agent include administration of neuroprotective agents, such as α-adrenoreceptor antagonist (e.g., α-dihydroergocryptine), NMDA antagonists (e.g., remacemide, 2-piperazinecarboxylic acid, N-indologlycinamide derivatives, spiro[benzo(b)thiophen-4(5H)] derivatives, eliprodil, dexanabinol, amantadine derivatives, dizocilpine, benzomorphan derivatives, aptiganel, (S)-α-phenyl-2-pyridine ethanamide dihyrochloride, 1-aminocyclopentanecarboxylic acid, and the like), sodium channel antagonists, glycine antagonists (e.g., glystasins), calcium channel antagonists (e.g., 3,5-pyridinedicarboxylic acid derivatives, conopeptides, 1-piperazineethanol, thieno [2,3-b]pyridine-5-carboxylic acid derivatives, nilvadipine, nisoldipine, tirilazad mesylate, 2H-1-enzopyran-6-ol, nitrone spin traps, iacidipine, iomeerzine hydrochloride, lemildipine, lifarizine, efonidipine, piperazine derivatives, and the like), calpain inhibitors, fibrinogen antagonists (e.g., ancrod), integrin antagonists (e.g., antegren), thromboxane $A_2$ antagonist (e.g., 9H-carbazole-9-propanoic acid derivatives, 5-Heptenoic acid derivatives, 1-azulenesulfonic acid derivatives, and the like), brain-derived neurotropic factor, adrenergic transmitter uptake inhibitor (e.g., 1-butanamine), endothelin A receptor antagonists (e.g., benzenesulfonamide derivatives), GABAA receptor antagonists (e.g., triazolopyrimidine derivatives, cyclohexaneacetic acid derivatives, and the like), GPIIb IIIa receptor antagonists, platelet aggregation antagonist (e.g., 2(1H)-quinolinone derivatives, 1H-pyrrole-1-acetic acid derivatives, coumadin, and the like), Factor Xa inhibitor, corticotropin releasing factor agonist, thrombin inhibitor (e.g., fraxiparine, dermatan sulfate, heparinoid, and the like), dotarizine, intracellular calcium chelators (e.g., BAPTA derivatives), radical formation antagonists (e.g., EPC-K1, 3-pyridinecarboxamide derivatives, superoxide dismutase, raxofelast, lubeluzole, 3H-pyrazol-3-one derivatives, kynurenic acid derivatives, homopiperazine derivatives, polynitroxyl albumin, and the like), protein kinase inhibitors (e.g., 1H-1,4-diazepine), nerve growth agonist, glutamate antagonist (e.g., cyclohexanepropanoic acid, riluzole, acetamide derivatives, and the like), lipid peroxidase inhibitors (e.g., 2,5-cyclohexadiene-1,4-dione derivatives), sigma receptor agonist (e.g., cyclopropanemethanamine derivatives), thyrotropin releasing hormone agonist (e.g., L-prolinamide, posatirelin, and the like), prolyl endopeptidase inhibitor, monosialoganglioside GM1, proteolytic enzyme inhibitor (e.g., nafamostat), neutrophil inhibitory factor, platelet activating factor antagonist (e.g., nupafant), monoamine oxidase B inhibitor (e.g., parafluoroselegiline, benzonitrile derivatives, and the like), PARS inhibitors, Angiotensin I converting enzyme inhibitor (e.g., perindopril, ramipril, and the like), acetylcholine agonist (e.g., pramiracetam), protein systhesis antagonist (e.g., procysteine), phosphodiesterase inhibitor (e.g., propentofylline), opioid kappa receptor agonist (e.g., 10H-phenothiazine-2-carboxamine derivatives), somatomedin-1, carnitine acetyltransferase stimulant (e.g., acetylcarnitine), and the like.

Still further treatments for which the invention dithiocarbamate-containing composition(s), which, when activated, are advantageously effective as nitric oxide scavenger(s) are employed in conjunction with the primary treating agent include administration of T cell inhibitors, such as synthetic leukocyte antigen derived peptides, interleukin-1 receptor antagonist, MG/AnergiX, anti-CD3 monoclonal antibodies, anti-CD23 monoclonal antibodies, anti-CD28 antibodies, anti-CD2 monoclonal antibodies, CD4 antagonists, anti-E selectin antibodies, MHC inhibitors, mycophenolate mofetil, and the like.

Additional treatments for which the invention dithiocarbamate-containing composition(s), which, when activated, are advantageously effective as nitric oxide scavenger(s) are advantageously employed in conjunction with the primary treating agent include administration of antimigraine agents, such as naratriptan, zolmitriptan, rizatriptan, quetiapine, Phytomedicine, (S)-fluoxetine, calcium channel antagonists (e.g., nimodipine/Nimotop, flunarizine, dotarizine, iomerizine HCl, and the like), α-dihydroergocryptine, 5-HT1 agonists, (e.g., Sumatriptan/Imitrex, Imigran, and the like), 5-HT1D agonists, 5-HT1A antagonists, 5-HT1B antagonists, 5-HT1D antagonists (e.g., 1H-indole-5-ethanesulfonamide derivatives, 1H-indole-5-methanesulfonamide, and the like), 2-thiophenecarboxamide, 3-piperidinamine, diclofenac potassium, dihydroergotamine, dolasetron mesilate, dotarizine, flupirtine, histamine-H3 receptor agonist, indobufen, 1-azuilenesulfonic acid derivatives, cholinesterase inhibitors, bradykinin antagonists, substance P antagonists (e.g., Capsaicin/Nasocap), piperazine derivatives, neurokinin 1 antagonists, metergoline, dopamine D2 antagonist (e.g., metoclopramide+lysine acetyl), enkephalinase inhibitors (e.g., neutral endopeptidase), 5-HT2 antagonists, 5-HT3 antagonists (e.g., Dolasetron mesilate, 4H-carbazol-4-one derivatives, and the like), tenosal, tolfenamic acid, cyclooxygenase inhibitors (e.g., carbasalate/carbaspirin calcium, tenosal, and the like), alpha adrenoreceptor antagonists (e.g., arotinolol, dihydroergocryptine, and the like), opioid agonists (e.g., flupirtine), beta adrenergic antagonists (e.g., propranolol), valproate semisodium, and the like.

Additional treatments for which the invention dithiocarbamate-containing composition(s), which, when activated, are advantageously effective as nitric oxide scavenger(s) are employed as nitric oxide scavenger(s) in conjunction with the primary treating agent include administration of antiarthritic agents, such as anti-CD4 monoclonal antibodies, phospholipase A1 inhibitor, loteprednol, tobramycin, combination of loteprednol and tobramycin, salnacedin, amiprilose, anakinra, anergiX, anti-B7 antibody, anti-CD3H, anti-gp39, anti-MHC MAbs, antirheumatic peptides, anti-Tac(Fv)-PE40, AP-1 inhibitors, purine nucleotide phosphorylase inhibitors, bindarit CD2 antagonist, campath-1H, CD4 antagonist, tumor necrosis factor antagonist (e.g., p80 TNFR, rhTNFbp, peptide T, CenTNF, thalidomide, and the like), cobra venom factor, interleukin 1a agonist (e.g., cytogenin), interleukin 2 receptor antagonist (e.g., dacliximab), ICAM 1 antagonist (e.g., enlimomab), interleukin 1 beta converting enzyme inhibitors (e.g., ICE-inhibitors), interferons, interleukin-10, interleukin 1 antagonist, interleukin-2 antagonist (e.g., sirolimus), phospholipase C inhibitor, neurokinin 1 antagonist, laflunimus, leflunomide, leucotriene antagonists, levamisole, LFA3TIP, macrocyclic lactone, MHC class II inhibitors, mizoribine, mycophenolate mofetil, NfκB inhibitors, peldesine, pidotimod, PNP inhibitors, reumacon, CD28 antagonist, roquinimex, subreum, tacrolimus, transforming growth factor beta agonist, methionine synthase inhibitors (e.g., vitamin B12 antagonist), adenosine A2 receptor agonist, CD5 antagonist (e.g., zolimomab), 5-lipoxygenase inhibitor (e.g., zileuton, tenidap, and the like), cyclooxygenase inhibitor (e.g., tenoxicam, talmetacin, piroxicam cinnamate, oxaprozin, mofezolac, nabumetone, flurbiprofen, aceclofenac, diclofenac, dexibuprofen, and the like), metalloproteinase inhibitor (e.g., TNF convertase inhibitors), phospholipase A2 inhibitor, leucotriene B4 antagonist, collagenase inhibitor, cyclooxygenase 2 inhibitor (e.g., meloxicam), thromboxane synthase inhibitor (e.g., curcumin), cysteine protease inhibitor, metalloproteinase inhibitor, lipocortins synthesis agonist (e.g., rimexolone, predonisolone 21-farnesylate, deflazacort, and the like), chelating agent (e.g., diacerein), elastase inhibitors, nitric oxide antagonists (e.g., hydroxocobalamin), stromelysin inhibitors, prostaglandin E1 agonist (e.g., misoprostol, misoprostol+diclofenac, and the like), dihydrofolate reductase inhibitor (e.g., trimetrexate), opioid antagonist (e.g., nalmefene), corticotropin releasing factor antagonist, proteolytic enzyme inhibitor (e.g., protease nexin-1), bradykinin antagonist (e.g., tachykinin antagonists), growth hormone antagonist (e.g., octreotide), phosphodiesterase IV inhibitor, gelatinase inhibitor, prostaglandin synthase inhibitors (e.g., sulfasalazine), and the like.

Additional treatments for which the invention dithiocarbamate-containing composition(s), which, when activated, are advantageously effective as nitric oxide scavenger(s) are employed in conjunction with the primary treating agent include administration of agents useful for the treatment of septic shock, such as angiogenesis inhibitors, bradykinin antagonists, complement factor inhibitors (e.g., C3 convertase inhibitor), C5a release inhibitors, dopamine agonists (e.g., dopexamine), elastase inhibitors, E selectin antagonists, farnesyltransferase inhibitors (e.g., RBE limonene), immunostimulants (e.g., lipid A vaccine, edobacomab, nebacumab, StaphGAM, diabodies, and the like), immunosuppressants (e.g., transcyclopentanyl purine analogues), interleukin 1 antagonists (e.g., interleukin 1receptors), interleukin 1 receptor agonists (e.g., anakinra), interleukin 1b antagonists (e.g., interleukin-1β), interleukin 1beta converting enzyme inhibitors (e.g., ICE-inhibitors), interleukin 8 antagonists (e.g., IL-8 receptor), interleukin 13 agonists (e.g., intereleukin-13), lipase clearing factor inhibitors, membrane permeability enhancers (e.g., Bactericidal Permeability Increasing protein/BPI), nitric oxide synthase inhibitors (e.g., L-NMMA, α-methyl-N-iminoethyl-ornithine, and the like), P2 receptor stimulants (e.g., ATP analogues), phosphatidic acid synthesis antagonists (e.g., lisofylline), phospholipase A2 inhibitors (e.g., acylpyrrole-alkanoic acid derivatives, indoleacetic acid derivatives, and the like), platelet activating factor antagonists (e.g., (2RS,4R)-3-(2-(3-pyridinyl)thiazolidin-4-oyl) indoles), prostacyclin agonists (e.g., taprostene), protein kinase C inhibitors, selectin antagonists (e.g., sulfated glycolipid cell adhesion inhibitors), FNF receptor-Ig, tumor necrosis factor antagonists (e.g., anti-TNF MAbs), tumor necrosis factor alpha antagonists, and the like.

Still further treatments for which the invention dithiocarbamate-containing composition(s), which, when activated, are advantageously effective as nitric oxide scavenger(s), are employed as nitric oxide scavenger(s) in conjunction with the primary treating agent include administration of agents for the treatment of multiple sclerosis, such as 4-aminopyridine, deoxyspergualin, ACTH, amantadine, antibody adjuvants (e.g., poly-ICLC), anti-cytokine monoclonal antibodies, anti-inflammatory agents, bacloten, bethanechol chloride, carbamazepine, carbohydrate drugs, clonazepam, CNS and immune system function modulators, cyclophosphamide, cyclosporine A, cytokines (e.g., IFN-α, alfaferone, IFN-β 1b, betaseron, TGF-β2, PEG-TGF-β2, betakine, IFN-β/Rebif, frone, interferon-β, IFN-β, and the like), CD4+T cell inhibitors (e.g., AnergiX), CD28 antagonists, growth factors (e.g., glial growth factor, GGF, nerve growth factors, TGF-β2, PEG-TGF-β2, betakine, and the like), humanized MAb (e.g., anti-IFN-γMAb, smart anti-IFN-γMAb, anti-Tac antibody, smart anti-Tac antibody, and the like), humanized anti-CD4 MAb (e.g., anti-CD4 MAb, centara, and the like), hydrolase stimulants (e.g., castanospermine), IFN-α, IFN-γ antagonists (e.g., anti-IFN-γMAb, smart anti-IFNγMAb, and the like), IL-2 antagonists (e.g., tacrolimus, Fujimycin, Prograf, IL-2 fusion toxin, DAB$_{389}$IL-2, and the like), IL-4 antagonists (e.g., IL-4 fusion toxin, DAB$_{389}$IL-4, and the like), immune-mediated neuronal damage inhibitors, immunoglobins, immunostimulants (e.g., poly-ICLC, edelfosine, ET-18-OCH-3, ET-18-OME, and the like), immunosuppressants (e.g., azathioprine, castanospermine, tacrolimus, FK-506, Fujimycin, Prograf, anti-leukointegrin MAb, primatized anti-CD4 antibody, linomide, roquinimex, transcyclopentanyl purine analogs, spanidin, 15-deoxyspergualin, deoxyspurgiline, gusperimus HCl, cyclosporine, SandImmune, IL-10, anti-TCR MAbs, anti-CD4 MAb, cantara, immunophilins, cyclophosphamide, and the like), integrin antagonists (e.g., anti-integrin monoclonal antibodies), interferon agonists, interferon-β-1b, isoprinosine, IV methylprednisolone, macrolides, MAO B inhibitors (e.g., selegiline, Parkinyl, and the like), methotrexate, mitoxantrone, muscarinic antagonists, oxybutinin chloride, oxygen free radical antagonists (e.g., tetrandrine, biobenzylisoquinoline alkaloid, and the like), phenoxybenzamine, phospholipase C inhibitors, photodynamic therapies (e.g., benzoporphyrin derivative (BPD)), platelet activating factor antagonists (e.g., ginkgolide B), potassium channel antagonists (e.g., aminodiaquine), propranolol, prostaglandin synthase inhibitors (e.g., sulfasalazine, salazosulfa-pyridine, azulfidine, salazopyrin, and the like), protease antagonists (e.g., ginkgolide B), recombinant soluble IL-1 receptors, spergualin analogs (e.g., spanidin, 15-deoxyspergualin, deoxyspurgiline, gusperimus HCl, and the like), selectin antagonists (e.g., lectin-1, recombinant IML-1, and the like), soluble TNF receptor I, TNF antagonists (e.g., thalidomide, TNF inhibitors, and the like), and the like.

Additional treatments for which the invention dithiocarbamate-containing composition(s), which, when activated, are advantageously effective as nitric oxide scavenger(s) are employed as nitric oxide scavenger(s) in conjunction with the primary treating agent include administration of organ transplantation agents, such as anti-CD25 MAbs, anti-Tac antibodies, anti-TNF MAb, apoptosin, azathioprines (e.g., imuran), complement inhibiting factors (e.g., CD59), cyclosporines (e.g., CsA), FK-506/rapamycin binding proteins (FKBP), glucocorticoids, humanized version of OKT3 (e.g., huOKT3-185), hydroorotate dehydrogenase inhibitors (e.g., Brequinar), orthoclone OKT3 (e.g., IgG2a anti-T cell murine monoclonal antibody, muromonab-CD3, and the like), rapamycins, streptomyces isolates, and the like.

Additional treatments for which the invention dithiocarbamate-containing composition(s), which, when activated, are advantageously effective as nitric oxide scavenger(s) are employed in conjunction with the primary treating agent include administration of agents for the treatment of systemic lupus erythematosus (SLE), such as androgen-derived steriods, anti-CD4 humanized antibodies, CD2 antagonists, cyclosporines (e.g., Sandimimune, cyclosporine analog, cyclosporin-G, NVal-CyA, and the like), cytokines (e.g., IL-4 fusion toxin), cytokine receptor antagonists (e.g., immunomodulatory cytokines), E-selentin antagonists (e.g., anti-E LAM), FK506/tacrolimus (e.g., Prograf), hypercalcemic agents, IFN-γ antagonists (e.g., anti-IFN-γMAb, smart anti-IFN-γMAb, and the like), IL-1β converting enzyme inhibitors (ICE), IL-2 produced by E. coli (e.g., celmoleukin, IL-2, Celeuk, and the like), immunoglobulins (e.g., anti-ELAM), immunostimulants (e.g., thymotrinan), immunosuppressants (e.g., Rapamycin, anti-CD4, T-cell inhibitor, anti-tac MAb, immunophilins, mycophenolate mofetil, IL-4 fusion toxin, trypanosomal inhibitory factor (TIF), Leflunomide, Spanidin, 15-deoxyspergualin, deoxyspurgiline, gusperimus hydrochloride, Roquinimex, linomide, and the like), immunotoxins (e.g.. Zolimomab aritox, Xomazyme-CD5 Plus, and the like), intravenous immunoglobulins, integrin antagonists (e.g., integrin blockers), Migis™ antibodies, monoclonal antibody therapeutics, murine MAb (e.g., anti-SLE vaccine, MAb 3E10, and the like), primatized anti-CD4 antibodies (e.g., CE9.1), protease inhibitors (e.g., matrix metalloprotease (MMP) inhibitors, stromelysin, and the like), protein synthesis antagonists (e.g., anti-CD6-bR, anti-T12-bR, oncolysin CD6, and the like), purine nucleoside phosphorylase inhibitors, selectin antagonists (e.g., Cylexin), spergualin analogues (e.g., Spanidin, 15-deoxyspergualin, deoxyspurgiline, gusperimus hydrochloride, and the like), T cell inhibitors (e.g., AnergiX), tumor necrosis factor (TNF) antagonists, and the like.

Additional treatments for which the invention dithiocarbamate-containing composition(s) are advantageously employed as nitric oxide scavenger(s) in conjunction with the primary treating agent include administration of agents for the treatment of Alzheimer's disease, such as ACh release enhancers (e.g., benzothiophene derivatives), acetylcholine release stimulants, AMPA agonists (e.g., AMAlex, Isoxazole compound series, and the like), AMPA GluR agonist (e.g., IDRA-21 [7-chloro-3-methyl-3,4-dihydro-2H-1,2,4-benzothiadiazinine]), anticholinesterases, Ca-antagonists (e.g., spider venom-derived ICM peptides and analogues, substituted 2-aminoindanes compound series, and the like), K-channel blockers (e.g., Trans-R-4-(4-methoxyphenyl-methyl) cyclohexylanine and analogues, margatoxin-based functional and/or structural analogues, and the like), muscarinic receptor agonists (e.g., Xanomeline), NMDA antagonists (e.g., certain indole derivatives, $(R-(R^1,S^1))-\alpha$-(4-hydroxyphenyl)-beta-methyl-4-(phenylmenthyl)-1-piperidinepropanol and analogues thereof, and the like), nicotinic AChR agonists (e.g., ABT-418 [isoxazole, 3-meth-5-(1-meth-2-pyrrolidinyl)], and the like), and the like.

Additional treatments for which the invention dithiocarbamate-containing composition(s) are advantageously employed nitric oxide scavenger(s) in conjunction with the primary treating agent include administration of agents for the treatment of psoriasis, such as 5-LO inhibitors (e.g., Lonapalene, Zileuton, epocarbazolin-A, and the like), 5-LO/CO inhibitors (e.g., Tenidap), angiogenesis inhibitors (e.g., platelet factor 4), anticancer antibiotic, anti-inflammatory cytochrome P450 oxidoreductase inhibitors, antiproliferative compounds (e.g., Zyn-Linker), arachidonic acid analogues, arachidonic acid antagonists (e.g., Lonopalene. triamcinolone acetonide with penetration enhancer Azone, betamethasone dipropionate steroid wipe, Halobetasol propionate, ultravate, Halometasone, Sicorten, and the like), beta-glucan receptor antagonists, betamethasone steroid wipes, calcium metabolic moderators (e.g., Tacalcitol, Bonealfa, Calcipotriol, Dovonex, and the like), CD4 binding inhibitors, cell adhesion inhibitors (e.g., selectin inhibitor), cellular aging inhibitors (e.g., Factor X), corticosteroids (e.g., Halobetasol propionate, ultravate, Halometasone, Sicorten, and the like), dihydrofolate reductase inhibitors (e.g., dichlorobenzoprim, methotrexate, methotrexate in microsponge delivery system, and the like), E-selectin inhibitors, endogenous active form of vitamin $D_3$ (e.g., Calcitriol), fibroblast growth factor antagonists (e.g., Saporin mitotoxin, Steno-Stat, and the like), fumagillin analogues, G-proteins and signal transduction compounds, gel formulations for acne (e.g., nicotinamide, Papulex, and the like), growth hormone antagonists (e.g., Octreotide, Sandostatin Lanreotide, angiopeptin, Somatuline, and the like), humanized antibodies (e.g., anti-CD4 antibody), hydroorotate dehydrogenase inhibitors (e.g., Brequinar sodium, bipenquinate, and the like), ICAM-1 inhibitors, IL-1 and other cytokine inhibitors (e.g., Septanil), IL-1 converting ezyme inhibitors, IL-1 receptor antagonists (e.g., Antril), IL-2 antagonists (e.g., Tacrolimus, Prograf, FK-506, and the like), IL-2 receptor-targeted fusion toxins, IL-8 receptors, immunostimulants (e.g., Thymopentin, Timunox, and the like), immunosuppressants (e.g., cyclosporine, Sandimmune, anti-CD11, Tacrolimus, Prograf, FK-506, FK-507, and the like), leukotriene antagonists, leukotriene B4 antagonists, leukotriene synthesis inhibitors, lipase clearing factor inhibitors (e.g., 1-docosanol, lidakol, and the like), lipid encapsulated reducing agent (e.g., Dithranol), liposomal gel (e.g., Dithranol), lithium succinate ointments (e.g., lithium salts, Efalith, and the like), octapeptide somatostatin analogues (e.g., Lanreotide, angiopeptin, Somatuline, and the like), PKC inhibitors, phospholipase A2 compounds, photodynamic anticancer agents (e.g., 5-aminolevulinic acid), photodynamic therapies (e.g., benzoporphyrin derivatives, synthetic chlorins, synthetic porphyrins, and the like), PKC inhibitors (e.g., Safingol, Kynac, and the like), platelet activating factor antagonists, platelet aggregation inhibitors (e.g., CPC-A), prostaglandin agonists (e.g., eicosapentaenoic acid+gamma-linolenic acid combination, Efamol Marine, and the like), protein kinase C (PKC) inhibitors, protein synthesis antagonists (e.g., Calcitriol, Namirotene, and the like), purine nucleoside phosphorylase inhibitors, radical formation agonists (e.g., benzoporphyrin derivatives), recombinant antileukoproteinases, retinoids, retinoid derivatives, rapamycin binding proteins (FKBP) (e.g., immunophilins), second generation monoaromatic retinoids (e.g., Acitretin, Neotigason, and the like), soluble IL-1, IL-4 and IL-7 receptors, somatostatin analogues (e.g., Octreotide, Sandostatin, and the like), superoxide dismutase, thymidylate synthase inhibitors, transglutaminase inhibitors, tyrphostin EGF receptor kinase blockers, VCAM-1 inhibitors, and the like.

Still further treatments for which the invention dithiocarbamate-containing composition(s), which, when advantageously effective as nitric oxide scavenger(s) are employed as nitric oxide scavenger(s) in conjunction with the primary treating agent include administration of agents for the treatment of diabetes, such as ACE inhibitors (e.g., captopril), amylin agonists and antagonists (e.g., Normylin™), autoimmune compounds, capsaicins (e.g., Zostrix-HP), domperidones (e.g., Motilium®, fluvastatins (e.g., Lescol), iloprost, insulin analogs (e.g., Nu-Insulin compounds, Humulin, Iletin, Humalog™, LYs-Pro, Amaryl, and the like), insulin-like growth factors, insulinotropins, nerve growth factors, oral hypoglycemics (e.g., glimepiride, Amaryl, acarbose, miglitol, recombinant yeast glucagon, GlucaGen™, NovoNorm™, glipizide, insulinotropin, and the like), platelet-derived growth factors (e.g., ZymoGenetics/NovoNordisk compounds), sulfonylureas (e.g., tolbutamide, acetohexamide, tolazamide, chlorpropramide, and the like), T cell approaches (e.g., anergize, Procept compounds, T cell Sciences compounds, and the like), tolrestats (e.g., Alredase®, and the like), and the like.

Additional treatments for which the invention dithiocarbamate-containing composition(s), which, when advantageously effective as nitric oxide scavenger(s) are employed as nitric oxide scavenger(s) in conjunction with the primary treating agent include the administration of agents for the treatment of stroke, such as Ancrod, 5-HT antagonists (e.g., Piperazine derivatives), 5-HT reuptake inhibitors (e.g., Milnacipran, Dalcipran, and the like), 5-HT agonists, 5-lipoxygenase inhibitors, ACH agonists (e.g., Pramiracetam, Choline-L-alfoscerate, L-alpha-glycerylphosphorylcholine, Delecit, and the like), adenosine agonists (e.g., arasine analogs), adenosine A1 receptor agonists (e.g., Azaisotere, 2-chloro-N-[4 (phenylthio)-1-piperidinyl] adenosine, and the like), adenosine reuptake inhibitors (e.g., Diphenyloxazole derivatives), adrenergic transmitter re-uptake inhibitors (e.g., Bifemelane, Alnert, Celeport, and the like), aldose reductase inhibitors (e.g., Spiro-3' pyrroline derivatives), alpha antagonists (e.g., Drotaverine acephyllinate, Depogen, and the like), alpha 2 agonists, Ancrod/Arvin, aspirin, benzothiazoles (e.g., Lubeluzole, and the like), benzodiazepine receptor antagonists (e.g., 3-oxadiazolyl-1,6-naphthyridine derivatives, Tetracyclic imidazodiazepineseries imidazenil, and the like), blood substitutes, bradykinin antagonists (e.g., Bradycor, Septicor, and the like), C5a release inhibitors (e.g., protein derivative), calcium antagonists (e.g., Lemildipine, Trimetazidine derivatives, Iomerizine, Diltiazem analog clentiazem maleate, and the like), calcium channel antagonists (e.g., nitrendipine-like compound diperdipine, Diltiazem derivative, tetrahydronaphthalene derivatives, fasudil, Eril, darodipine, dazodipine, Dihydropyridine, Lacidipine, Nilvadipine, and the like), calpain inhibitors, carnitine palmitoyl-transferase inhibitors, carvedilol, cell adhesion molecular technology, cerebral calcium antagonist vasodilators (e.g., Nimodipine, Nimotop, and the like), cholinesterase inhibitors (e.g., indole and indazole derivatives, Tacrine analogs, and the like), complement factor inhibitors (e.g., protein derivative TP16, compinact A, compinact C, Factor D inhibitors, soluble, recombinant MCP-based complement inhibitors, and the like), complement inhibitors, coronary vasodilators (e.g., Nicorandil, Adancor, and the like), cytidyl diphosphocholine/citicholines, cytokines, Dexanabiol, dopamine agonists, endothelin antagonists, endothelin receptor antagonists, excitatory amino acid agonists (e.g., acylated polyamine analogs, N-(4-hydroxyphenylpropa-noyl)spermine analogs, and the like), excitatory amino acid antagonists (e.g., Tryptophan, 4,6-disubstituted stroke & kynurenine derivatives, and the like), glutamate antagonists (e.g., Kainate, quisqualate, and the like), glutamate receptor antagonists (e.g., Araxin compounds, Quinoxaline derivative, and the like), glycine antagonists, glycine NMDA agonists (e.g., 3-hydroxy-2,5-dioxo-1H-benz[b]azepines), glycine NMDA associated antagonists (e.g., Strychnine-insensitive glycine binding site of NMDA receptor, Glystasins, eliprodil, and the like), growth factor antagonists (e.g., non-peptide indolocarbazole neutrophic molecules, and the like), GPIIb/IIIa antagonists, heparin, hydroxyl radical formation inhibitors (e.g., homopiperazine derivatives), hypocalcemic agents (e.g., calcitonin peptide, related to hCGRP peptide), ICAM-1 compounds (e.g., Enlimomab), Interleukin-1 antagonists (e.g., cyclic nitrones), iron-dependent lipid peroxidation inhibitors (e.g., 2-(amino-methyl) chromans), lactic acid accumulation/inhibitors, lipid peroxidase inhibitors (e.g., Idebenone, Avan, and the like), methyltransferase stimulants (e.g., 4-methyl benzenesulfonate, ademetionine sulfate tosilate, Ceritan, and the like), monoamine oxidase B inhibitors (e.g., Lazabemide), nadroparin (e.g., Fraxiparin), nafronyl/naftidrofuryl (e.g., Praxilene), nerve growth factor agonists (e.g., small molecule compounds, monosialoganglioside GM1, and the like), neuronal calcium channel blockers, NMDA antagonists (e.g., Spiroisoindoles/dizocilpine derivatives, Oxindole compound, Sialic acid derivative, N-palmitoyl-Betaethylglycoside neuraminic acid, Dextrorphan, Ifenprodil analogue eliprodil, Lipophilic molecules, Remacemide, and the like), NMDA antagonist-partial agonists (e.g., Conantokin G peptide), NMDA channel blockers (e.g., Aptiganel, CERESTAT, and the like), NMDA receptor antagonists, nootropic/acetylcholine agonists (e.g., Oxiracetam, Neuractiv, and the like), norepinephrine inhibitors (e.g., Midalcipran), N-type calcium channel antagonists, opioid antagonists (e.g., Nalmefene, nalmetrene, Cervene, Incystene, and the like), opioid kappa receptor agonists (e.g., acrylacetamide enadoline), organoselenims (e.g., Ebselen), oxygen scavengers (e.g., Tirilazad mesylate, Lazaroids, Freedox, and the like), PAF antagonists (e.g., nupafant), partial glycine NMDA agonists (e.g., ACPC), peptide/GPIIb/IIIa antagonists (e.g., Integrelin), peptidic neuron-specific calcium channel antagonists, phosphodiesterase inhibitors (e.g., Xanthine derivatives, propentofylline, Hoe-285, Hextol, and the like), plasminogen activators (e.g., r-ProUK (recombinant pro-urokinase), platelet-activating factor antagonists, platelet aggregation antagonists (e.g., cilostazol, peptide agents, GPIIb-IIIA inhibitor, and the like), platelet aggregation inhibitors (e.g., Diaminoalkanioic acid derivatives), potassium channel agonists (e.g., Nicorandil, Adancor, and the like), prolyl endopeptidase (PEP) inhibitors, protein kinase C inhibitors (e.g., monosialoganglioside derivatives), proteolytic enzyme inhibitors (e.g., Protease nexin-1, Incyte, Nafamostat, Duthan, Futhan, and the like), pyrimidine derivatives, Quinolizine derivatives, recombinant tissue plasminogen activators (e.g., alteplase, Activase, and the like), Schwann cell derived molecules/promoters, sigma receptor antagonists (e.g., tetrahyropyridinyl-isoxazolines), sodium/calcium channel modulators (e.g., Lifarizine), sodium channel antagonists, streptokinase (e.g., Streptase), superoxide dismutase stimulants (e.g., PEG conjugated enzyme superoxide dismutase/Dismutec, PEG-SOD, and the like), thrombin inhibitors, (e.g., non-peptide), thromboxane synthase inhibitors (e.g., Linotroban), thyrotropin-releasing hormone agonists (e.g., TRH agonists, Protirelin analogthymoliberin, and the like), ticlopidine (e.g., Ticlid), TRH agonists (e.g., Thyrotropin releasing hormones), trilazard, urokinase (e.g., Abbokinase), warfarin (e.g., Coumadin), and the like.

Accordingly, presently preferred indications for treatment in accordance with the present invention include septic shock, ischemia, ulcers, inflammatory bowel disease(s) (e.g., ulcerative colitis) diabetes, arthritis, neurodegenerative diseases (e.g., Alzheimer's disease, Parkinson's disease, and multiple sclerosis) cirrhosis or allograft rejection, hemodialysis, stroke, skin diseases (e.g., psoriasis), and the like.

In accordance with a particular aspect of the present invention, the invention dithiocarbamate-containing composition(s) is administered as a protected form of a nitric oxide scavenging agent in combination with one or more of the above-described agents, and optionally further in conjunction with an antibiotic (e.g., gentamicin, tobramycin, amikacin, piperacillin, clindamycin, cefoxitin or vancomycin, or mixtures thereof), a vasoactive agent (e.g., a catecholamine, noradrenaline, dopamine or dobutamine), or mixtures thereof. In this way, the detrimental side effects of many of the above-noted pharmaceutical agents and/or the indications they are designed to address (e.g., systemic hypotension) can be prevented or reduced by co-administration of a combination reagent that releases a nitric oxide scavenger.

When used to release an active nitric oxide scavenger, typical daily doses of the invention disulfide derivatives of dithiocarbamates, in general, lie within the range of from about 10 μg up to about 100 mg per kg body weight, and, preferably within the range of from 50 μg to 10 mg per kg body weight and can be administered up to four times daily. The daily IV dose lies within the range of from about 1 μg to about 100 mg per kg body weight, and, preferably, within the range of from 10 μg to 10 mg per kg body weight.

In general, the dosage of the invention disulfide derivatives of dithiocarbamates for release of a nitric oxide scavenger in the practice of the present invention falls in the range of about 0.01 mmoles/kg body weight of the subject/hour up to about 0.5 mmoles/kg/hr.

In accordance with another embodiment of the present invention, there are provided methods for the in vivo reduction of cyanide levels in a subject. Invention methods comprise administering to a subject an effective amount of at least one physiologically compatible compound having the structure I as described herein for in vivo reacting with cyanide in the subject.

In accordance with another embodiment of the present invention, there are provided combination methods for reducing cyanide levels in a subject. Invention methods comprise administering to a subject an effective amount of at least one physiologically compatible compound having the structure I (as described hereinabove) so as to react with cyanide in the subject, in combination with at least one active agent selected from:

alpha-ketoglutaric acid and sodium thiosulfate, hydroxocobalamin, organophosphate antidote (e.g., atropine, oximes, and the like), oxygen therapy, resealed erythrocytes containing rhodanese and sodium thiosulfate, methemoglobin former(s) (e.g., Lily Cyanide Antidote Kit, amylnitrite, sodium nitrite and sodium thiosulfate, primaquine phosphate, 6-methoxy-8-(6-diethylaminohexylamino) lepidine dihydrochloride, p-aminooctoylphenome, p-aminopropiophenone, hydroxylamine, 4-methylaminophenol, and the like), In accordance with another embodiment of the present invention, there are provided methods for treating a subject having elevated circulating levels of cyanide, said method comprising administering to said subject an effective amount of at least one physiologically compatible dithiocarbamate derivative having the structure I (as described herein) for in vivo reacting with cyanide.

In accordance with yet another embodiment of the present invention, there are provided methods for reducing the toxicity of cyanide in a subject exposed thereto, said method comprising administering to said subject an effective amount of at least one physiologically compatible compound having the structure I (as described herein) for in vivo reacting with cyanide in the subject.

In accordance with still another embodiment of the present invention, there are provided methods for the treatment of cyanide poisoning of a subject, said method comprising administering to said subject an effective amount of at least one physiologically compatible compound having the structure I (as described herein) for in vivo binding of cyanide.

As readily recognized by those of skill in the art, cyanide toxicity and/or cyanide poisoning is associated with a variety of exposures, e.g., ingestion of certain foods (e.g., extracts of plants containing cyanogenic glycosides, such as cassava) or drugs (e.g., sodium nitroprusside, laetrile), inhalation of industrial gases (e.g., gases produced by electroplating operations), combustion byproducts (e.g., combustion products of polymers prepared from acrylonitrile, methacrylonitrile, allylnitrile, crotononitrile, fumaronitrile, and the like), agents of warfare (e.g., cyanide gas), and the like.

Since individual subjects may present a wide variation in severity of symptoms and each drug has its unique therapeutic characteristics, the precise mode of administration and dosage employed for each subject is left to the discretion of the practitioner. In general, when the invention disulfide derivatives of dithiocarbamate(s) are used to react with cyanide, the dosage employed in the practice of the present invention falls in the range of about 0.01 mmoles/kg body weight of the subject/hour up to about 0.5 mmoles/kg/hr. Typical daily doses of the invention dithiocarbamate-containing composition(s) when used as cyanide scavengers, in general, lie within the range of from about 10 μg up to about 200 mg per kg body weight, and, preferably within the range of from 50 μg to 10 mg per kg body weight and can be administered up to four times daily. The daily IV dose lies within the range of from about 1 μg to about 100 mg per kg body weight, and, preferably, within the range of from 10 μg to 20 mg per kg body weight.

Subjects contemplated for treatment in accordance with the present invention include mammals (such as humans, canines, felines, bovine, ovine, rodents, and the like), fowl (e.g., chicken, turkey, and the like), and so on.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

In accordance with yet another embodiment of the present invention, there are provided compositions comprising a pharmaceutically acceptable carrier, at least one physiologically compatible compound having structure I as described herein for in vivo reacting with cyanide, and at least one of:

alpha-ketoglutaric acid and sodium thiosulfate, hydroxocobalamin, organophosphate antidote, oxygen therapy, resealed erythrocytes containing rhodanese and sodium thiosulfate, methemoglobin former(s), and the like.

In accordance with another embodiment of the present invention, there are provided methods for the in vivo reduction of free iron ion levels in a subject by administering to the subject an effective amount of at least one physiologically compatible compound having the structure I (as described herein) so as, when activated, to bind free iron ions in the subject.

As used herein, the phrase "free iron ions" refers to transient iron species which are not stably incorporated into a biological complex (e.g., hemoglobin, ferritin, and the like). Scavengers contemplated for use herein are highly selective for "free iron ions", relative to other forms of iron present in a physiological system.

In accordance with another embodiment of the present invention, there are provided methods for treating subjects having elevated circulating levels of free iron ions. Invention methods comprise administering to a subject an effective amount of at least one physiologically compatible compound having the structure I (as described herein) so as, when activated, to bind free iron ions in the subject.

In accordance with yet another embodiment of the present invention, there are provided methods for treating overproduction of free iron ions in a subject by administering to the subject an effective amount of at least one physiologically compatible compound having the structure I (as described herein), which, when activated, binds free iron ions in the subject.

The presence of elevated iron levels in a subject is associated with a wide range of disease states and/or indications, such as, for example, hereditary conditions (e.g., thalassemia, sickle cell anemia, hereditary hemochromatosis, hereditary spherocytosis, hemolytic disease of the newborn, and the like), afflictions related to invasive exchange of body fluids (e.g., repeated blood transfusions, hemodialysis, cardiopulmonary bypass, ischemic/reperfusion injury, dietary iron uptake, latrogenic iron uptake, intramuscular iron dextran, and the like).

Additional indications associated with elevated levels of free iron ions include anthracycline anti-cancer therapy, inflammation (e.g., liver inflammation, renal inflammation, and the like), , septic shock, hemorrhagic shock, anaphylaetic shock, toxic shock syndrome, arthritis (e.g., rheumatoid arthritis), ulcers, ulcerative colitis, inflammatory bowel disease, gastritis, adult respiratory distress syndrome, asthma, cachexia, transplant rejection, myocarditis, multiple sclerosis, diabetes mellitus, autoimmune disorders, eczema, psoriasis, glomeruionephritis, heart failure, heart disease, atherosclerosis, Crohn's disease, dermatitis, urticaria, isahemia, cerebral ishemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Parkinson's disease, Huntington's disease epilepsy, neurodegenerative disorders, gastrointestinal motility disorders, obesity, hyperphagia, ischemia/reperfusion injury, allograft rejection, solid tumors (e.g., neuroblastoma), malaria, cancers (e.g., breast, melanoma, carcinoma, hematologic cancers, and the like), Alzheimer's disease, infection (including bacterial, viral, fungal and parasitic infections), myelofibrosis, lung injury, graft-versus-host disease, head injury, CNS trauma, cirrhosis, hepatitis, renal failure, liver disease (e.g., chronic hepatitis C), drug-induced lung injury (e.g., paraquat), transplant rejection and preservation, bum, administration of cytokines, overexpression of cytokines, encephalomyelitis, meningitis, pancreatitis, peritonitis, vasculitis, lymphocytic choriomeningitis, uveitis, ileitis, myasthenia gravis (MG), ophthalmic diseases, post-angioplasty, restenosis, angina, coronary artery disease, stroke, chronic fatigue syndrome, photoaging, photodamage, and the like.

With particular reference to cytokine therapy, the invention method will find widespread use because cytokine therapy (with consequent induction of release of free iron ions) is commonly used in the treatment of cancer and AIDS patients. Side effects due to the induction of free iron ion release are problems commonly associated with cytokine therapy (see, for example, Lissoni et al in J. Biol. Regulators Hemeostatic Agents 7:31–33 (1993)). Thus, a large patient population exists which will benefit from invention methods.

Presently preferred indications for treatment in accordance with the present invention include administration of interleukin-1 (IL-1), administration of interleukin-2 (IL-2), administration of interleukin-6 (IL-6), administration of interleukin-11 (IL-11), administration of interleukin-12 (IL-12), administration of tumor necrosis factor (TNF), administration of interferon-alpha (IF-α) or interferon-gamma (IF-γ), arthritis, asthma, Alzheimer's disease, Parkinson's disease, multiple sclerosis, cirrhosis or allograft rejection. Especially preferred indications for treatment in accordance with the present invention include release of free iron ions associated with cytokine therapy.

As readily understood by those of skill in the art, a wide variety of agents and/or conditions induce release of free iron ions. Thus, invention compositions can advantageously be included in combination with treating agents for such indications. Thus, for example, invention compositions can be combined with anti-inflammatory agents, immunosuppressants, antistroke agents, anticancer agents, thrombolytic agents, neuroprotectants, nitric oxide synthase inhibitors, anti-migraine agents, and the like.

Examplary treatments for which the above-described combinational therapy for binding of free iron ions employing invention compositions is contemplated include:

inflammatory disease therapy (e.g., employing disease-modifying agents (such as antimalarials, methotrexate, sulfasalazine, mesalamine, azathioprine, 6-mercaptopurine, metronidazole, injectable and oral gold, D-penicillamine, and the like), corticosteroids, non-steroidal antiinflammatory drugs (such as acetominophen, aspirin, sodium salicylate, magnesium salicylate, choline magnesium salicylate, salicylsalicylic acid, ibuprofen, naproxen, diclofenac, diflunisal, etodolac, fenoprofen calcium, fluriprofen, piroxicam, indomethacin, ketoprofen, ketorolac tromethamine, meclofenamate, meclofenamate sodium, mefenamic acid, nabumetone, oxaprozin, phenyl butyl nitrone (PBN), sulindac, tolmetin, and the like), and the like), immunosuppression (e.g., employing one or more agents such as cyclosporin A, OKT3, FK506, mycophenolate mofetil (MMF), azathioprine, corticosteroids (such as prednisone), antilymphocyte globulin, antithymocyte globulin, and the like), stroke therapy (e.g., employing one or more agents such as fibrinolytic agents (such as streptokinase, acylated plasminogen-streptokinase complex, urokinase, tissue plasminogen activator, and the like), employing monoclonal antibodies directed against leukocyte adhesion molecules (such as intercellular adhesion molecule-1 (ICAM-1), CD18, and the like), hemodilution therapy (employing modified hemoglobin solutions such as diaspirin crosslinked hemoglobin), employing growth factors (such as basic fibroblast growth factor (bFGF), transforming growth factor-beta 1 (TGF-β1), and the like), employing glutamate antagonists (such as lamotrigine, dizolcilpine maleate (MK 801), BW619C89, BW1003C87, and the like), employing NMDA antagonists (such as CGS 19755 (Selfotel), aptiganel hydrochloride, dextrorphar, d-CPPene, and the like), employing GABA agonists (such as muscimol), employing free radical scavengers (such as allopurinol, S-PBN, 21-aminosteroids, tocopherol, superoxide dismutase, dexanabinol (HU-211), selenium, carotenoids, and the like), idebenone, ticlopidine, lovastatin, citicoline, and the like), anti-cancer therapy (e.g., employing one or more agents such as alkylating agents (such as mechlorethamine, chlorambuccil, ifosfamide, melphalan, busulfan, carmustine, lomustine, procarbazine, dacarbazine, cisplatin, carboplatin, and the like), antimetabolites (such as methotrexate, mercaptopurine, thioguanine fluorouracil, cytarabine, and the like), hormonal agents (such as testosterone propionate, fluoxymesterone, flutamide, diethylstilbestrol, ethinyl estradiol, tamoxifen, hydroxyprogesterone caproate, medroxyprogesterone, megestrol acetate, and the like), adrenocorticosteroids (such as prednisone), aromatase inhibitors (such as amino glutethimide), leuprolide, goserelin acetate, biological response modifiers (such as interferon-α2a, interferon-α2b, interleukin-2, and the like), peptide hormone inhibitors (such as octreotide acetate), natural products (such as vinblastine, vincristine, vinorelbine, paclitaxel, dactinomycin, daunorubicin, idarubicin, doxorubicin, etoposide, plicamycin, mitomycin, mitoxantrone, bleomycin, hydroxyurea, mitotane, fludarabine, cladribine, and the like), supportive agents (such as allopurinol, mesna, leucovorin, erythropoietin, filgrastim, sargramostim, and the like), and the like, thrombolytic therapy for acute myocardial infarction (e.g., employing agents such as streptokinase, tissue plasminogen activator (t-PA), anistreplase, and the like), administration of neuroprotective agents, such as α-adrenoreceptor antagonist (e.g., (α-dihydroergocryptine), NMDA antagonists (e.g., remacemide, 2-piperazinecarboxylic acid, N-indologlycinamide derivatives, spiro[benzo(b) thiophen-4(5H)] derivatives, eliprodil, dexanabinol, amantadine derivatives, dizocilpine, benzomorphan derivatives, aptiganel, (S)-α-phenyl-2-pyridine ethanamide dihyrochloride, 1-aminocyclopentanecarboxylic acid, and the like), sodium channel antagonists, glycine antagonists (e.g., glystasins), calcium channel antagonists (e.g., 3,5-pyridinedicarboxylic acid derivatives, conopeptides, 1-piperazineethanol, thieno[2,3-b] pyridine-5-carboxylic acid derivatives, nilvadipine, nisoldipine, tirilazad mesylate, 2H-1-enzopyran-6-ol, nitrone spin traps, iacidipine, iomeerzine hydrochloride, lemildipine, lifarizine, efonidipine, piperazine derivatives, and the like), calpain inhibitors, fibrinogen antagonists (e.g., ancrod), integrin antagonists (e.g., antegren), thromboxane $A_2$ antagonist (e.g., 9H-carbazole-9-propanoic acid derivatives, 5-Heptenoic acid derivatives, 1-azulene-sulfonic acid derivatives, and the like), brain-derived neurotropic factor, adrenergic transmitter uptake inhibitor (e.g., 1-butanamine), endothelin A receptor antagonists (e.g., benzenesulfonamide derivatives), GABA A receptor antagonists (e.g., triazolopyrimidine derivatives, cyclohexaneacetic acid derivatives, and the like), GPIIb IIIa receptor antagonists, platelet aggregation antagonist (e.g., 2(1H)-quinolinone derivatives, 1 H-pyrrole-1-acetic acid derivatives, coumadin, and the like), Factor Xa inhibitor, corticotropin releasing factor agonist, thrombin inhibitor (e.g., fraxiparine, dermatan sulfate, heparinoid, and the like), dotarizine, intracellular calcium chelators (e.g., BAPTA derivatives), radical formation antagonists (e.g., EPC-K1, 3-pyridinecarboxamide derivatives, superoxide dismutase, raxofelast, lubeluzole, 3H-pyrazol-3-one derivatives, kynurenic acid derivatives, homopiperazine derivatives, polynitroxyl albumin, and the like), protein kinase inhibitors (e.g., 1H-1,4-diazepine), nerve growth agonist, glutamate antagonist (e.g., cyclohexanepropanoic acid, riluzole, acetamide derivatives, and the like), lipid peroxidase inhibitors (e.g., 2,5-cyclohexadiene-1,4-dione derivatives), sigma receptor agonist (e.g., cyclopropanemethanamine derivatives), thyrotropin releasing hormone agonist (e.g., L-prolinamide, posatirelin, and the like), prolyl endopeptidase inhibitor, monosialoganglioside GM1, proteolytic enzyme inhibitor (e.g., nafamostat), neutrophil inhibitory factor, platelet activating factor antagonist (e.g., nupafant), monoamine oxidase B inhibitor (e.g., parafluoroselegiline, benzonitrile derivatives, and the like), PARS inhibitors, Angiotensin I converting enzyme inhibitor (e.g., perindopril, ramipril, and the like), acetylcholine agonist (e.g., pramiracetam), protein systhesis antagonist (e.g., procysteine), phosphodiesterase inhibitor (e.g., propentofylline), opioid kappa receptor agonist (e.g., 10H-phenothiazine-2-carboxamine derivatives), somatomedin-1, carnitine acetyltransferase stimulant (e.g., acetylcarnitine), and the like.

inhibition of nitric oxide synthase enzymes (e.g., employing arginine analogs (such as L-$N^G$-methylarginine, L-$N^G$-nitroarginine, L-$N^G$-aminoarginine, L-iminoethylornithine, ε-N-iminoethyl-L-lysine, L-$N^G$-nitroarginine methyl ester, L-$N^G$-hydroxyl-$N^G$-methylarginine, L-$N^G$-methyl-$N^G$-methylarginine, L-thiocitrulline, L-S-methylthiocitrulline, L-S-ethylisothiocitrulline, S-ethylisothiocitrulline, aminoguanidine, S-methyl isothiourea sulfate, and the like), heme ligands (such as 7-nitroindazole, 7,7,8,8-tetramethyl-o-quinodimethane, imidazole, 1-phenylimidazole, 2-phenylimidazole, and the like), calmodulin antagonists (such as chlorpromazine, W-7, and the like), and the like);

administration of antimigraine agents, such as naratriptan, zolmitriptan, rizatriptan, quetiapine, Phytomedicine, (S)-fluoxetine, calcium channel antagonists (e.g., nimodipine/Nimotop, flunarizine, dotarizine, iomerizine HCl, and the like), α-dihydroergocryptine, 5-HT1 agonists, (e.g., Sumatriptan/Imitrex, Imigran, and the like), 5-HT1D agonists, 5-HT1A antagonists, 5-HT1B antagonists, 5-HT1D antagonists (e.g., 1H-indole-5-ethanesulfonamide derivatives, 1H-indole-5-methanesulfonamide, and the like), 2-thiophenecarboxamide, 3-piperidinamine, diclofenac potassium, dihydroergotamine, dolasetron mesilate, dotarizine, flupirtine, histamine-H3 receptor agonist, indobufen, 1-azulenesulfonic acid derivatives, cholinesterase inhibitors, bradykinin antagonists, substance P antagonists (e.g., Capsaicin/Nasocap), piperazine derivatives, neurokinin 1 antagonists, metergoline, dopamine D2 antagonist (e.g., metoclopramide+lysine acetyl), enkephalinase inhibitors (e.g., neutral endopeptidase), 5-HT2 antagonists, 5-HT3 antagonists (e.g., Dolasetron mesilate, 4H-carbazol-4-one derivatives, and the like), tenosal, tolfenamic acid, cyclooxygenase inhibitors (e.g., carbasalate/carbaspirin calcium, tenosal, and the like), alpha adrenoreceptor antagonists (e.g., arotinolol, dihydroergocryptine, and the like), opioid agonists (e.g., flupirtine), beta adrenergic antagonists (e.g., propranolol), valproate semisodium, and the like.

In accordance with a particular aspect of the present invention, the disulfide derivative of dithiocarbamate is administered in combination with a cytokine (e.g., IL-1, IL-2, IL-6, IL-11, IL-12, TNF or interferon-γ), an antibiotic (e.g., gentamicin, tobramycin, amikacin, piperacillin, clindamycin, cefoxitin or vancomycin, or mixtures thereof), a vasoactive agent (e.g., a catecholamine, noradrenaline, dopamine or dobutamine), or mixtures thereof. In this way, the detrimental side effects of many of the above-noted pharmnaceutical agents (e.g., induction of release of free iron ions) can be prevented or reduced by the invention dithiocarbamate-containing scavenger. Thus, a patient being treated with any of the above-described agents could be monitored for evidence of elevated free iron ion levels. At the first evidence of such elevated levels of free iron ions, co-administration of a suitable dose of the above-described disulfide derivative of dithiocarbamate scavenger could be initiated, thereby alleviating (or dramatically reducing) the side-effects of the primary therapy.

In accordance with yet another embodiment of the present invention, there are provided compositions comprising an anthracycline anti-cancer agent and a disulfide derivative of dithiocarbamate having the structure I, as described above, which, when activated, is effective as a scavenger of free iron ions.

Since individual subjects may present a wide variation in severity of symptoms and each drug has its unique therapeutic characteristics, the precise mode of administration and dosage employed for each subject is left to the discretion of the practitioner. In general, the dosage of the invention dithiocarbamate compounds when employed as an iron ion scavenger in the practice of the present invention falls in the range of about 5 mg–18.5 g/day. Presently preferred modes of administration are oral, topical, by inhalation or by injection.

Those of skill in the art will recognize that compositions comprising the invention dithiocarbamate(s) in the various methods described herein can be delivered in a variety of ways, such as, for example, orally, intravenously, subcutaneously, parenterally, rectally, by inhalation, and the like.

Since individual subjects may present a wide variation in severity of symptoms, and each drug has its unique therapeutic characteristics for the particular condition being treated, the precise mode of administration, dosage employed and treatment protocol for each subject is left to the discretion of the practitioner.

In accordance with still another embodiment of the present invention, there are provided physiologically active composition(s) comprising a compound having the structure I, (as described above), in a suitable vehicle rendering said composition amenable to oral delivery, transdermal delivery, intravenous delivery, intramuscular delivery, topical delivery, nasal delivery, and the like. The composition(s) may optionally further contain one or more "active agent" (as described herein).

Depending on the mode of delivery employed, the above-described compositions can be delivered in a variety of pharmaceutically acceptable forms. For example, the above-described compositions can be delivered in the form of a solid, solution, emulsion, dispersion, micelle, liposome, and the like.

Pharmaceutical compositions of the present invention can be used in the form of a solid, a solution, an emulsion, a dispersion, a micelle, a liposome, and the like, wherein the resulting composition contains one or more of each of the nitric oxide scavenging and therapeutically active compounds contemplated for use in the practice of the present invention, as active ingredients thereof, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compounds (i.e., "therapeutic agents" and nitric oxide scavenging compounds (e.g., compounds of structure I as described herein)) are included in the pharmaceutical composition in an amount sufficient to produce the desired effect upon the target process, condition or disease.

Pharmaceutical compositions containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions. In addition, such compositions may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compositions contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

Compounds contemplated for use in the practice of the present invention may also be formulated for topical administration, for example, as a skin lotion, suntan lotion, cosmetic lotion, moisturizer, lip balm, eye makeup, face cream, and the like. A typical formulation includes one or more compounds as described herein, in combination with moisturizers, antioxidants, and the like.

Moisturizers contemplated for use in the above-described topical formulations include occlusive moisturizers, such as, for example, hydrocarbon oils and waxes, petroleum jelly, silicone oils, silicone derivatives, vegetable and animal fats, cocoa butter, mineral oil, fatty acids, fatty alcohols, lanolin, phospholipids, and the like; humectants, such as, for example, glycerin, honey, lactic acid, sodium lactate, ceramide, urea, propylene glycol, sorbitol, pyrrolidone carboxylic acid, glycolic acid, gelatin, vitamins, proteins, and the like; hydrophilic matrices, such as, for example, hyaluronic acid, colloidal oatmeal, and the like; essential fatty acids (e.g., Dermasil), elastin, niosomes, and the like.

Antioxidants contemplated for use in the above-described topical formulations include superoxide dismutase, catalase, glutathione peroxidase, glutathione reductase, γ-tocopherol, α-tocopherol, ubiquinol 10, ubiquinone 10, ascorbic acid, uric acid, glutathione, and the like.

Commonly used active ingredients in sunscreen products include para-aminobenzoic acid (PABA), benzophenone, padimate O, cinnamates, homosalate, oxybenzone, octylsalicylates, and the like. Exemplary sunscreen products include Shade SPF15 (available from Schering-Plough Corp., Memphis, Tenn.), Pre-Sun SPF15 cream (available from Westwood-Bristol Myers, Buffalo, N.Y.), Sundown SPF15 (available from Proctor and Gamble, Cincinnati, Ohio), Bullfrog SPF36 (available from Chattem, Inc., Chattanooga, Tenn.), Daylong 16 (available from SpirigAG, CH-Egerkingen, an emulsion gel containing 70% water, ethanol, phospholipids, carbopol, sorbitol, silicone, amphisol, cetyl alcohol, tocopherol, triethanolamine, preservatives, and preparations with white petroleum jelly as vehicle, and the like.

Commonly used active ingredients in skin care products include alphahydroxy acids, tocopherol sorbate, ascorbate, glycolic acid, and the like.

The invention will now be described in greater detail by reference to the following non-limiting examples.

EXAMPLE 1

Synthesis of Disulfide Dithiocarbamates

1A Synthesis of N-Methyl-D-glucamine Dithiocarbamate Disulfide

To a solution of N-methyl-D-glucamine dithiocarbamate (MGD) (7.64 g or 26 mmol) in 30 ml water was added dropwise, under constant stirring with magnetic stirrer, a solution of iodine (3.3 g or 13 mmol) in 50 ml absolute ethanol. The iodine color disappeared immediately. An additional amount of ethanol (150 ml) was added at the end of the reaction. The reaction mixture was kept at 4° C. for four hours and the precipitate was filtered, washed with 2×50 mL ethanol and air dried for 24 hrs. After additional vacuum drying for 16 hrs, it produced 5.5 g of N-methyl-D-glucamine dithiocarbamate disulfide (MGDD). Yield 78%, the structure was confirmed by $^1$H NMR at 500 Mhz $(D_2O)\delta$; 4.43 (2H, m); 4.35 (2H; m); 4.20 (1H, m); 4.04 (1H, m); 3.9–3.7 (12H, m); 3.7–3.6 (1H, m); 3.60 (3H, s) and by Mass analysis: calculated mass for $C_{16}H_{32}N_2O_{10}S_4$-(M+Na$^+$): 563. Found: 563.

1B Synthesis of Pyrrolidine Dithiocarbamate Disulfide

Figure 9:
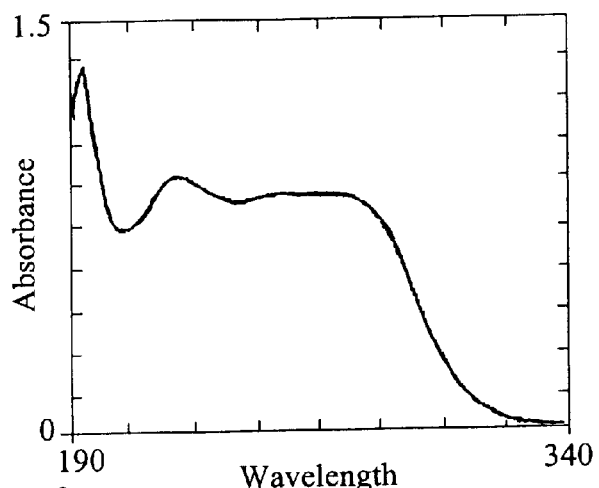
FIG. 9 is an illustration of the UV spectrum of Pyrrolidine dithiocarbamate disulfide measured on Hewlett Packard 8451A Diode Array Spectrophotometer. Scanning wavelength 190 nm–340 nm; Cell length 1 cm. The background is measured against 1 mL deionized water+1 $\mu$l acetone. Added 1 $\mu$l stock solution pyrrolidine dithiocarbamate in acetone to a final concentration 20 $\mu$g/mL.

To a solution of 3 g (18.3 mmol) pyrrolidine dithiocarbamate ammonium salt in 30 mL water is added with constant stirring to form a solution of 2.32 (9.1 mmol) iodine in 25 mL absolute ethanol. The reaction is very fast and the iodine color disappears instantly. At the end of the reaction, the product is filtered, washed with 3×20 mL water and dried overnight under vacuum. Yield 2.6 g (97%) of pyrrolidine dithiocarbamamte disulfide. $^1$H NMR, 500 Mhz, $(CDCl_3)\delta$; 3.88 (8H, m); 2.15 (4H; m); 2.02 (4H, m). Mass analysis: calculated for $C_{10}H_{16}N_2S_4$-(M+H)+: 293. Found: 393 See UV spectrum (FIG. 9).

EXAMPLE 2

Figure 2:
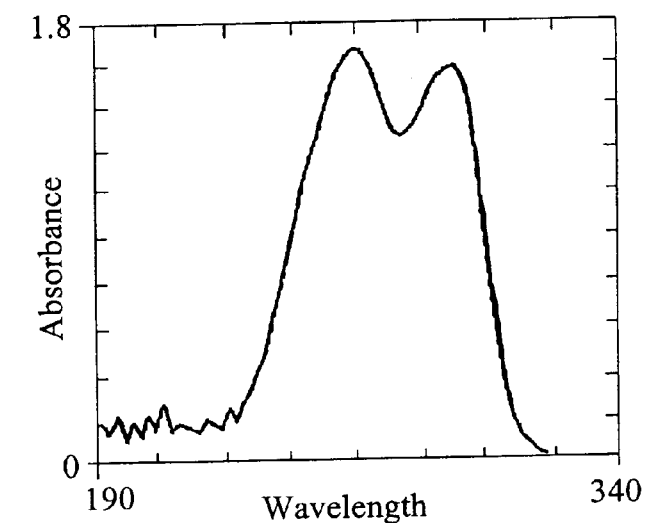
FIG. 2 is an illustration of the UV spectrum of N-methyl-D-glucamine dithiocarbamate disulfide (MGDD) (20 $\mu$g/mL)in the presence of L-cysteine (5 mg/mL). The spectrum was recorded with a scan range of 190 nm to 340 nm. The spectrum is identical to that of N-methyl-D-glucamine dithiocarbamate (MGD) alone (not shown).

Conversion of N-methyl-D-glucamine Dithiocarbamate Disulfide to N-methyl-D-glucamine Dithiocarbamate by the Addition of L-cysteine The UV spectrum of MGDD as shown in FIG. 1 does not have a distinct maximum, which is typical for this class of compounds (see, for example, H. P. Koch, *J. Chem. Soc.*, 401, 1949). A freshly prepared solution of L-cysteine (5 mg/mL) in 60 mM HEPES buffer, pH 7.4 was transferred into a UV cell (cell length 1 cm) and the absorbance of this solution was recorded as a background. Immediately after the addition of MGDD (final concentration of 20 µg/mL), the spectrum was recorded with a scan range of 190 nm to 340 nm. The addition of L-cysteine to the an MGDD solution transformed the spectrum immediately from that shown in FIG. 1 to that shown in FIG. 2; the latter is a characteristic spectrum for N-methyl-D-glucamine dithiocarbamate (MGD). The results illustrate that MGDD can readily be converted into its starting material, MGD, by the addition of simple, biocompatible thiol reducing agents.

EXAMPLE 3

Fast Reaction Between N-methyl-D-glucamine Dithiocarbamate Disulfide and Potassium Cyanide.

Figure 3:
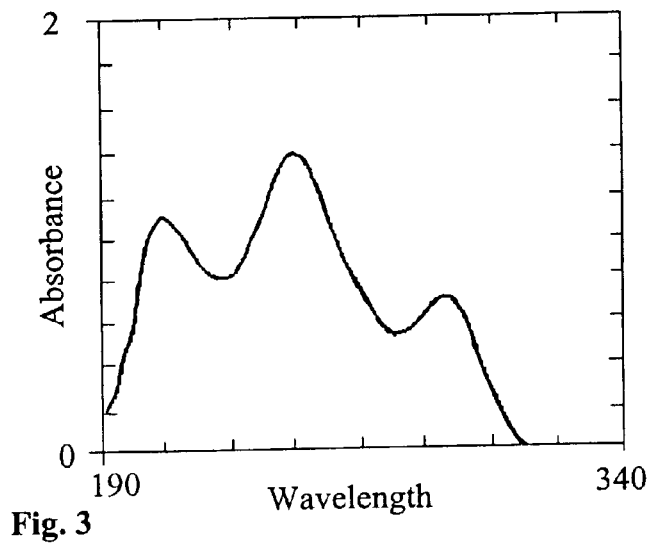
FIG. 3 is an illustration of the UV spectrum of MGDD in the presence of potassium cyanide (KCN). A solution of KCN (3 mg/ml) in water was transferred into the cuvette and its absorbance was recorded as a background. A solution of MGDD in deionized water was added to the KCN solution to a final concentration of 20 $\mu$g/mL. The spectrum was recorded immediately after the mixing.

Upon addition of potassium cyanide to the MGDD solution, the spectrum of MGDD (shown in FIG. 1) was changed immediately into the spectrum as shown in FIG. 3. This change is indicative of a fast reaction between dithiocarbamate disulfides and cyanide to produce CNS anion and dithiocarbamate monosulfide (see, for example, J. C. D. Brand, et al., *J. Chem. Soc.*, 15, 1956), suggesting that MGDD could be effective against cyanide poisoning.

EXAMPLE 4

Synthesis of L-Proline Dithiocarbamate Disulfide

To a solution of L-proline dithiocarbamate (2.2 g or 9.46 mmol) in 40 mL water was added a solution of iodine (1.2 g or 4.7 mmol) in 17 mL absolute ethanol with constant stirring. The reaction reached completion within minutes as indicated by the disappearance of the iodine color. After the addition of acetone (180 ml), the product was crystallized in a few minutes. the product was filtered after two hours, then washed with 3×20 mL acetone and air dried overnight. Yield 1.7 g (85%) of L-Proline dithiocarbamate disulfide (L-PDD). The structure was confirmed by Mass analysis: calculated mass for $C_{12}H_{14}N_2Na_2O_4S_4$-$(M+Na^+)$:447. Found: 447. The UV spectru of L-proline dithiocarbamate disulfide was similar to that of N-methyl-D-glucamine dithiocarbamate disulfide (as shown in FIG. 1). The solution behavior of L-PDD, particularly in reference to its reaction with L-cysteine and potassium cyanide was similar to that of MGDD as well.

EXAMPLE 5

Effect of L-proline Dithiocarbamate on the Survival of Diabetic-prone BB Rats

In vivo, L-proline dithiocarbamate disulfide is reduced chemically by simple thiol molecules such as L-cysteine or glutathione to produce monomeric L-proline dithiocarbamate (L-PD). We tested the effectiveness of the oral administration of (L-PD) for the treatment of diabetic-prone BB rats, an animal model that is widely used for type I insulin-dependent diabetes. Type I diabetes is an autoimmune disease. the pathogenesis of this disease remains unclear although there is ample evidence for increased NO production at early stages of the disease (see, for example, G. M. Piper, *Hypertension*, 31:1047–1060, 1998).

Figure 4:
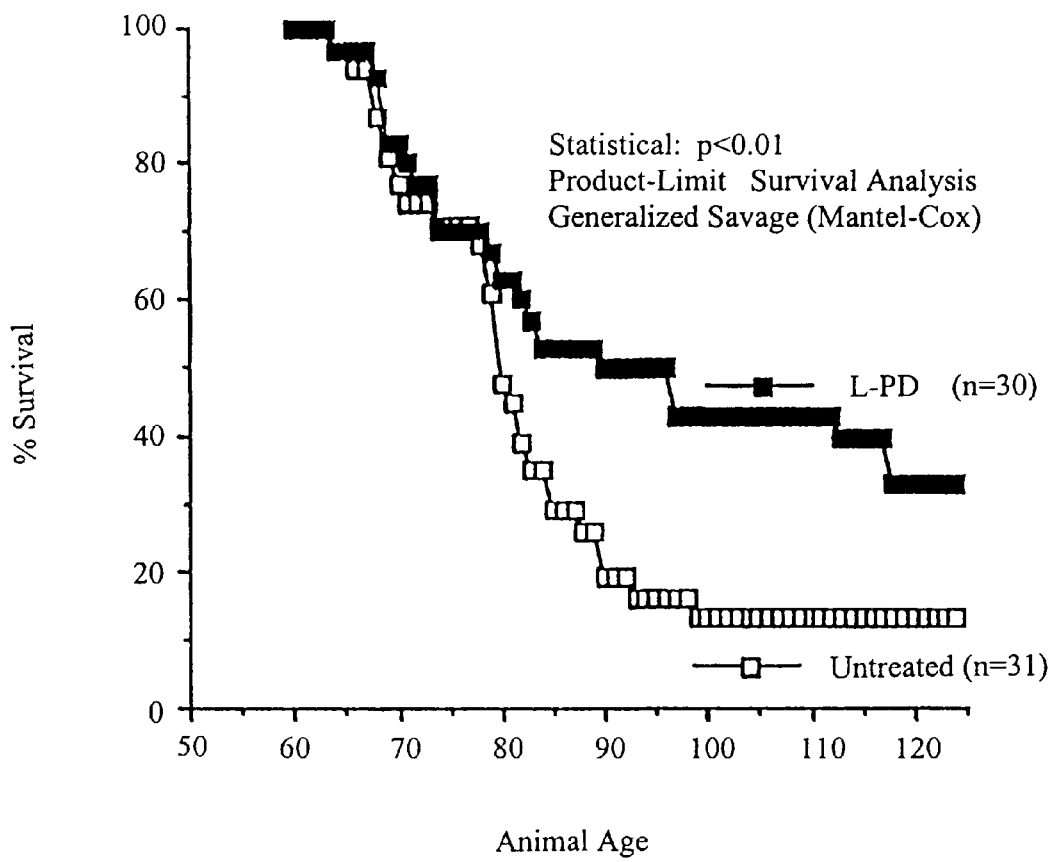
FIG. 4 is a graph illustrating the effects of oral administration of L-proline dithiocarbamate on the survival of diabetic-prone BB rats. The percentage of survival was plotted against the age of the animals over 125 days. The treated group (n=30) (■) received 5 mg/ml monomeric L-proline dithiocarbamate in drinking water, while the untreated group (n=31) (□) received only water. The improvement in survival in the treated group was statistically significant compared to the untreated group.

Male, diabetic-prone BB rats (n=61, 250–280 g) were used for the study. The rats were distributed between untreated and L-PD treated groups. The treated group received 5 mg/ml L-PD in drinking water. The treatment started when the animals were 2 months old and continued until they were 4 months old. Chronic treatment with L-PD had no apparent effect on water consumption of diabetic—prone BB rats throughout the course of the study. As shown in FIG. 4, the oral administration of L-PD for 2 months improved the survival of diabetic-prone BB rats. At the end of the experiments, whereas only 10 percent of untreated animals survived, more than 30 percent of treated animals survived. Percent survival was calculated by Product-Limit Survival Analysis Generalized Savage (Mantel-Cox) with $p<0.01$.

EXAMPLE 6

The Treatment with N-methyl-D-glucamine (MD) Reduces Bacterial Translocation after Endotoxemia in Rats Endotoxemia is known to promote gut barrier failure and bacterial translocation (BT) by upregulating inducible nitric oxide synthase (iNOS) in the gut (see, for example, J. E. Parrillo, *N. Engl. J. Med.*, 3328:1471–1477, 1993). Experiments were conducted to test whether administration of MGD could protect the intestinal mucosa of rats from NO-mediated damage after lipopolysaccharide (LPS) challenge so as to reduce the incidence of BT in rats.

Sprague-Dawley rats were randomized to receive either 450 mg MGD or equal volume of normal saline (NS) via subcutaneously placed osmotic pump (Alzet CA) for 18 hours prior to intraperitoneal injection of 10 mg/kg LPS. Bacterial translocation in vivo was measured by quantitative cultures of blood, mesenteric lymph nodes, liver, and spleen 24 hours after LPS challenge. The results are summarized in Table 1 below. The treatment with MGD was found to significantly reduce the incidence of bactermia and BT in rats. The study suggests that MGD and its related compounds can prevent LPS induced gut barrier failure by removing excessive NO.

TABLE 1

Effect of Nitric Oxide on Bacterial Translocation after LPS challenge in vivo

| | NORMAL SALINE (N = 32) | NOX (N = 29) Pre treat |
|---|---|---|
| Bacterial Translocation (mesenteric lymph node) | *56.2% | 17.2% |
| % Positive blood cultures | **28.1% | 0% |

*p = 0.004 Chi square
**p = 0.008 Fischer Exact Mean

EXAMPLE 7

Administration of N-methyl-D-glucamine Dithiocarbamate (MGD) Protects Against Hepatocellular Injury After Lipopolysaccaharide (LPS) challenge The experimental design was similar to that of Example 6. Sprague-Dawley rats were treated with MGD via subcutaneously implanted osmotic pump for 18 hours and then injected intraperitoneally with LPS. The hepatocellular injury was assessed by liver function tests, and by light and transmission electron microscopy. Then RNAs for inducible NO synthase (iNOS) and IL-6 were measured by reverse transcriptase-PCR. TNF-alpha protein was identified by immunohistochemistry.

The results showed that the treatment with MGD decreased blood levels of ornithine carbamoyl transferase and aspartate trasaminase. In addition, the levels of TNF-alpha, and IL-6 were elevated in the untreated group, but not in the treated group. Kupffer cell proliferation and neutrophil infiltration were increased significantly in the control group, but not in the MGD-treated group. Histological analysis revealed that MGD prevented heptocellular necrosis induced by LPS challenge. It is concluded that MGD could potentially be useful for treatment of septic shock and other cardiovascular diseases characterized by excessive NO production.

EXAMPLE 8

Treatment In vivo with MGD-Fe Complex Prevents Diabetes-induced Endothelial Dysfunction Substantial evidence exists that diabetes results in impaired endothelial function, although factors that contribute to the development of this defect are still not known. In this study, experiments were carried out to test whether chronic treatment in vivo with MGD-Fe complex prevents endothelial dysfunction in diabetes in rats. Sprague-Dawley rats were made diabetic by an intravenous injection of stretozotocin (STZ). A subgroup of control of diabetic animals received twice daily subcutaneous injections of 8-mg/kg MGD/Fe (10:1 ratio) beginning at 48 hours post-STZ and throughout 8 weeks of diabetes. At the end of 8 weeks, blood glucose and glycosylated hemoglobin was significantly elevated in diabetic rats while serum insulin levels were reduced. Treatment with MGD-Fe complex did not alter glucose or insulin levels in control or diabetic rats; however, total glycosylated HB was partially reduced compared to untreated rats.

In isolated tissue baths, relaxation to the endothelium-dependent vasodilator, acetylcholine, was impaired in diabetic aortic rings while relaxation to nitroglycerin was unaltered. In contrast in diabetic rats, the treatment with MGD-Fe complex prevented the impairment in endothelium-dependent relaxation while having no effect on relaxation induced by nitroglycerin. These data suggest that MGD-Fe prevents endothelial dysfunction in diabetic rats.

EXAMPLE 9

Combinational Treatment with MGD and Cyclosporine (Low-dose) Prolongs Allograft Survival The role of NO in allograft rejection is well established. For example, NO is produced during allograft rejection by the expression of inducible NO synthase in the rejecting heart (see, for example, X. Yang, et al., *J. Clin. Invest.*, 94:714–721, 1994 and N. K. Worral, et al., *J. Exp. Med.*, 191:63–70, 1995). The introduction of cyclosporine A (CsA) in 1983 represented a major breakthrough in the transplantation field. Since then, CsA has been established to be an effective immunosuppressive agent against allograft rejection and other inflammatory diseases. However, despite its benefits for transplant patients, CsA still has major shortcomings. Toxicity to the kidney and liver is a known limitation of CsA, and long-term use of this drug presents the risk of graft failure because the drug accelerates endothelial dysfunction, resulting in arteriosclerosis. Experiments were performed to determine whether the combination therapy with MGD and subtherapeutic doses of CsA can prolong organ survival.

Lewis (Lew) and Wistar-Furth (WF) rat strains, which have a complete genetic disparity at both the major and minor histcompatibility loci, were used for this study. Lewis rats underwent either isogeneic (Lew-Lew) or allogenic (WF-Lew) heterotopic cardiac transplantation by standard methods. Allograft rejection was defined by loss of palpable contractile activity and was confirmed by direct inspection at laparatomy. The survival of the cardiac allograft in the WF-Lew group averaged about 7 days. MGD (5 mg/ml) in drinking water increased allograft survival time to 12 days. Low-dose CsA (2.5 mg/kg i.m.) increased allograft survival time to 23 days. However, the combinational therapy that used low-dose CsA (2.5 mg/kg, i.m. daily) and MGD (5 mg/ml in the drinking water daily) resulted in remarkably long-term graft survival of more than 200 days. The data support the contention that the daily oral administration of MGD and daily intramuscular injection of low-dose CsA improved greatly the survival of transplanted heart, and reduced the toxicity associated with CsA.

EXAMPLE 10

Treatment with L-proline Dithiocarbamate (L-PD) Reduces Joint Swelling in the Rat Model of Adjuvant-induced Arthritis The overproduction of NO plays a role in pathogenesis of arthritis (see, for example, A. R. Amin et al., *Curr. Opin. Rheumatol,* 10:263–268, 1998). In this study, the therapeutic effects of L-PD on the treatment of the adjuvant-induced model of arthritis in rats were evaluated.

Figure 5:
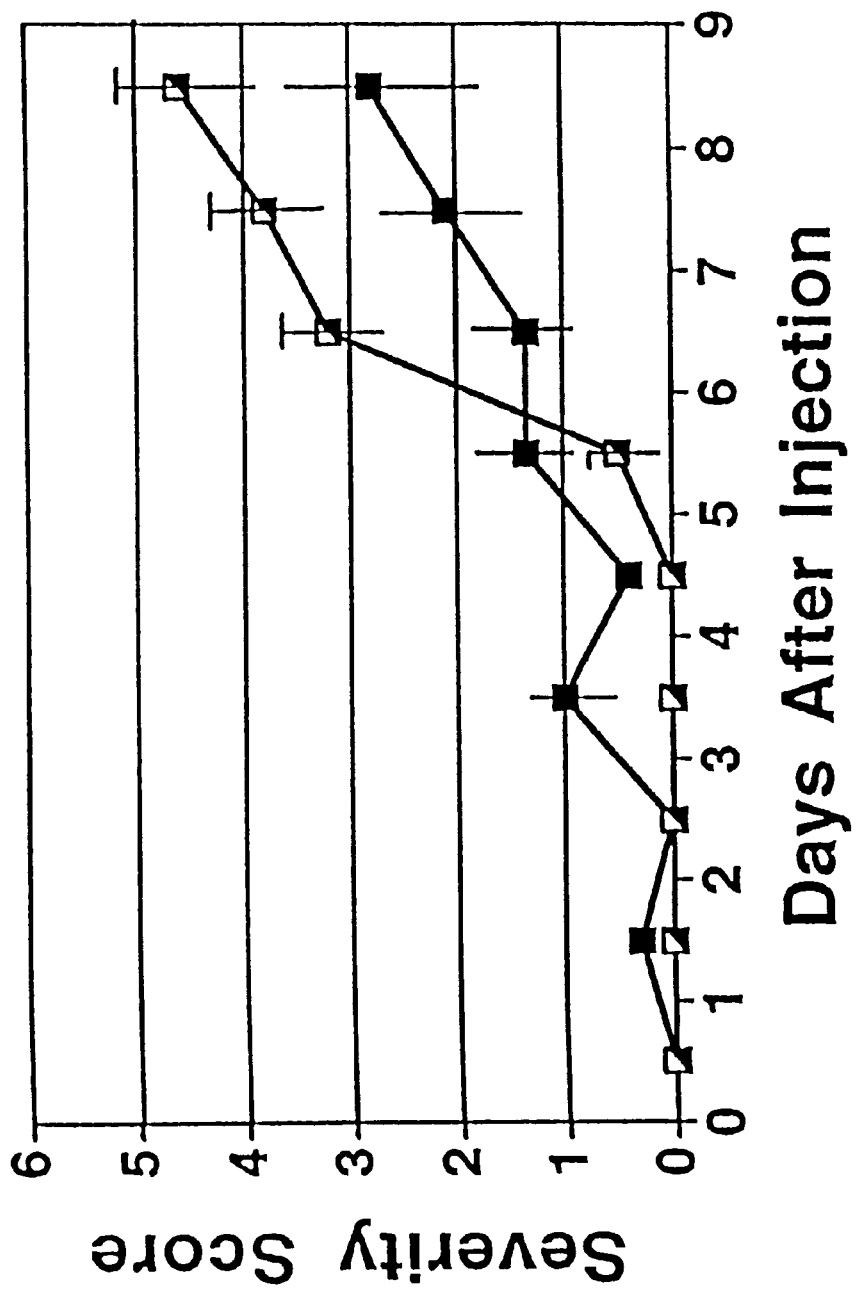
FIG. 5 is a graph showing the severity score of rats over a time course of 8 days post-injection with heat killed M tuberculosis (5 mg/ml) in the left footpad. The test rats (■) were given L-PD in drinking water (10 mg/ml). Control rats (▨) received only distilled water for drinking. Beginning on day 6, the left foot of the animals was scored for the development of arthritic disease using the following system: 0=no redness or inflammation, 1=one area of redness or inflammation on the foot less than 2 mm in diameter, 3=partial redness/inflammation of the footpad, 4=all of footpad red or inflamed, 5=criteria of 4 plus at least one toe red or inflamed, and 6=criteria of 4 plus toes inflamed and deformed (toes curling under footpad).
Figure 6:
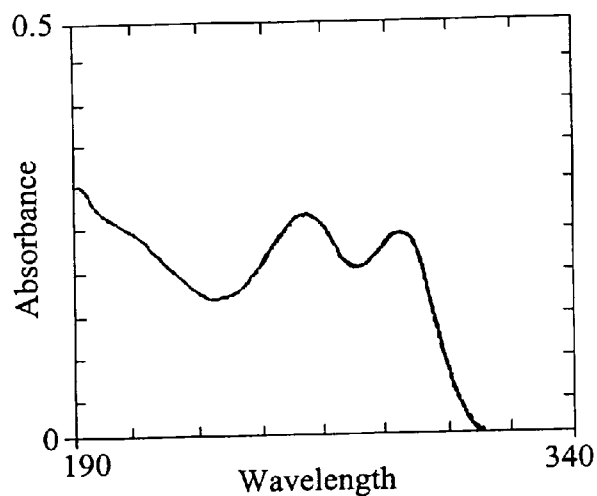
FIG. 6 is an illustration of the UV spectrum of N-methyl-D-glucamine dithiocarbamate (sodium salt, MGD) measured on Hewlett Packard 8451A Diode Array Spectrophotometer, Scanning wavelength 190 nm; cell length 1 cm; solvent—deionized water, concentration 5 $\mu$g/mL.
Figure 7:
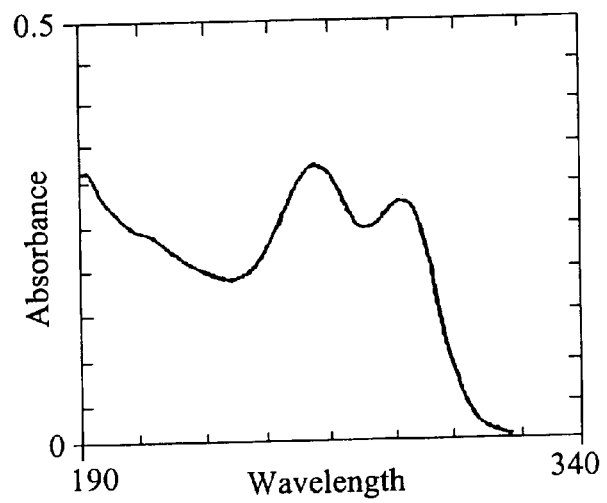
FIG. 7 is an illustration of the UV spectrum of L-proline dithiocarbamate (disodium salt) measured according to the method of FIG. 6.
Figure 8:
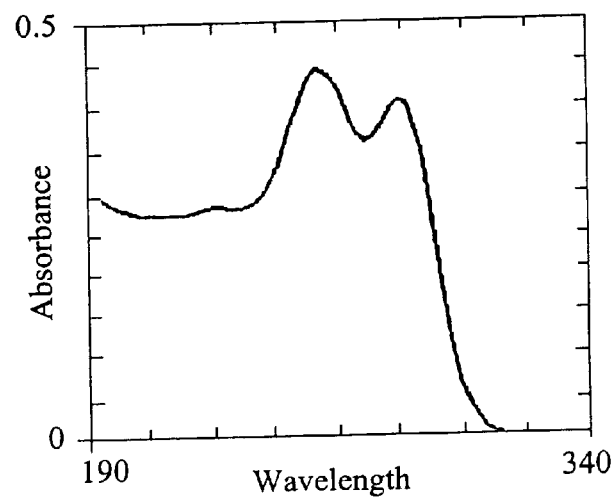
FIG. 8 is an illustration of the UV spectrum of pyrrolidine dithiocarbamate (ammonium salt) measured according to the method of FIG. 6.

After the subcutaneous injection in the right footpad of a suspension in mineral oil of heat killed M. tuberculosis on day 1, the Lewis rats were separated into two groups (n=9); one given L-PD (10 mg/ml) in the drinking water and the other given only distilled water. Beginning on day 6, the left foot of the animals was scored for the development of arthritic disease using the following system: 0=no redness or inflammation, 1=one area of redness or inflammation on the foot less than 2 mm in diameter, 3=partial redness/inflammation of the footpad, 4=all of footpad red or inflamed, 5=criteria of 4 plus at least one toe red or inflamed, and 6=criteria of 4 plus toes inflamed and deformed (toes curling under footpad). As shown in FIG. 5, the oral administration of L-PD significantly reduced the severity score of the inflammation in the left footpad, suggesting an anti-inflammatory effect of L-PD on this adjuvant-induced model of arthritis in rats.

EXAMPLE 11

Figure 10:
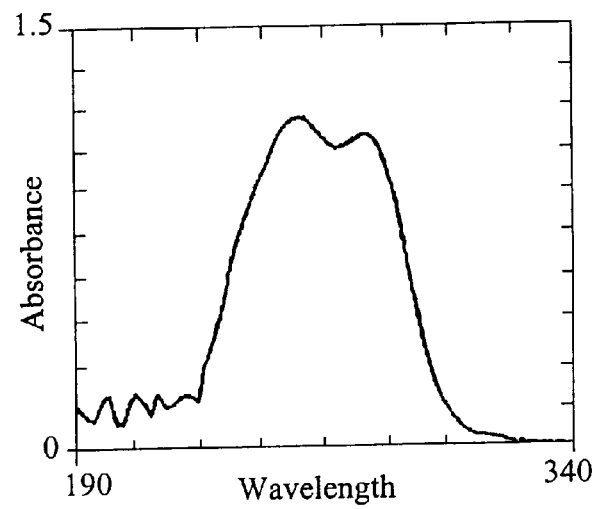
FIG. 10 is an illustration of the UV spectrum measured on Hewlett Packard 845 1A Diode Array Spectrophotometer. Scanning wavelength 190 nm–340 nm. One mL freshly prepared solution of L-cysteine (5 mg/mL) in 60 mM HEPES buffer, pH=7.4 is transferred into the UV cell (cell length 1 cm) plus 1 $\mu$l acetone and the absorbance of this solution is measured as a background. Added 1 $\mu$l stock solution of Pyrrolidine dithiocarbamate disulfide (PDD) in acetone to the cuvette—final concentration of PDD is 20 $\mu$g/mL. After mixing the UV spectrum is measured immediately.

Conversion of Pyrrolidine Dithiocarbamate Disulfide to Pyrrolidine Dithiocarbamate by the Addition of L-cysteine A freshly prepared solution of L-cysteine (5 mg/mL) in 60 mM HEPES buffer, pH 7.4 was transferred into a UV cell (cell length 1 cm) plus 1 μl acetone and the absorbance of this solution was recorded as background. Immediately after the addition of Pyrrolidine dithiocarbamate disulfide (PDD) (final concentration of 20 μg/mL), the spectrum was recorded with a scan range of 190 nm to 340 nm. The addition of L-cysteine to the PDD solution transformed the spectrum immediately from that shown in FIG. 9 to that shown in FIG. 10 The results illustrate that PDD can readily be converted into its starting material, pyrrolidine dithiocarbamate by the addition of simple, biocompatible thiol reducing agents.

EXAMPLE 12

Fast Reaction Between Pyrrolidine Dithiocarbamate and Potassium Cyanide

Figure 11:
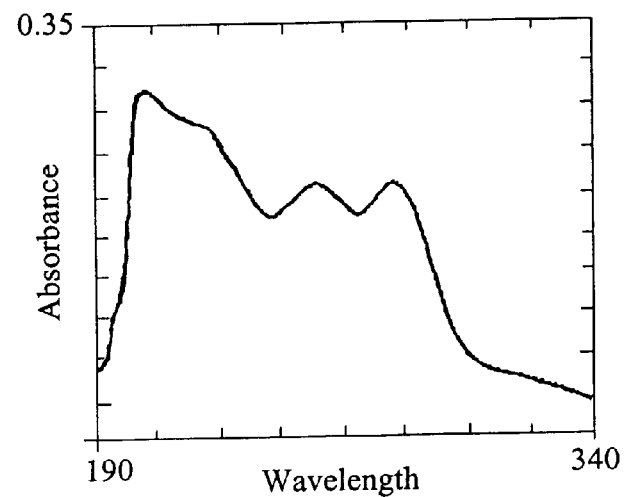
FIG. 11 is an illustration of the UV spectrum measured on Hewlett Packard 8451A Diode Array Spectrophotometer. Scanning wavelength 190 nm–340 nm; cell length 1 cm. One mL solution of KCN (5 mg/mL) in deionized water is transferred into the cuvette and measured as a background. Added 1 $\mu$l solution of pyrrolidine dithiocarbamate disulfide in methanol to a final concentration 5 $\mu$g/mL. After mixing the UV spectrum is measured immediately.

Upon addition of potassium cyanide to the PDD solution, the spectrum of PDD (shown in FIG. 9) was changed immediately into the spectrum as shown in FIG. 11. This change is indicative of a fast reaction between dithiocarbamate disulfides and cyanide to produce CNS anion and dithiocarbamate monosulfide, suggesting that PDD could be effective against cyanide poisoning.

While the invention has been described in detail with reference to certain preferred embodiments thereof, it will be understood that modifications and variations are within the spirit and scope of that which is described and claimed.

That which is claimed is:

1. A pharmaceutical composition comprising:
   i. a pharmaceutically acceptable carrier,
   ii. a compound having the structure (I) as follows:

$$R_1R_2N\text{---}C(S)\text{---}S\text{---}S\text{---}(S)C\text{---}NR_2R_1 \quad (I)$$

wherein:
   each of $R_1$ and $R_2$ is independently selected from a $C_1$ up to $C_{18}$ alkyl, substituted alkyl, a cycloalkyl, a substituted cycloalkyl, heterocyclic, a substituted heterocyclic, an alkenyl, a substituted alkenyl, an alkynyl, a substituted alkynyl, an aryl, a substituted aryl, an heteroaryl, a substituted heteroaryl, an alkylaryl, a substituted alkylaryl, an arylalkyl, and a substituted arylalkyl, or
   wherein $R_1$ and $R_2$ cooperate to form a 5-, 6- or 7-membered ring including N, $R_1$ and $R_2$ or $R_1$ or $R_2$ is a divalent moiety selected from the group consisting of an alkylene, a substituted alkylene, an oxyalkylene, a substituted oxyalkylene, an alkenylene, a substituted alkenylene, an arylene, a substituted arylene, an alkarylene, a substituted alkarylene, an aralkylene and a substituted aralkylene, wherein said divalent moiety serves as the same substituent for two dithiocarbamate structures, thereby linking said structures together so as to form a bis(dithiocarbamate), and iii. optionally, a biocompatible reducing agent to reduce the disulfide bond in the dithiocarbamate.

2. The composition according to claim 1 wherein:

each of $R_1$ and $R_2$ is independently selected from a $C_1$ up to $C_{12}$ alkyl, a substituted alkyl, an alkenyl, a substituted alkenyl, an alkynyl and a substituted alkynyl, wherein the substituents are selected from the group consisting of carboxyl, —C(O)H, oxyacyl, phenol, phenoxy, pyridinyl, pyrrolidinyl, amino, amido, hydroxy, nitro and sulfuryl.

3. The composition according to claim 1 wherein $R_1$ is selected from a $C_2$ up to $C_8$ unsubstituted alkyl, and an alkyl having a substitutent selected from the group consisting of carboxyl, acetyl, pyridinyl, pyrrolidinyl, amino, amido, hydroxy and nitro substituents, and $R_2$ is selected from a $C_1$ up to $C_6$ unsubstituted or substituted alkyl, or $R_2$ can cooperate with $R_1$ to form a 5-, 6- or 7-membered ring including N, $R_2$ and $R_1$.

4. The composition according to claim 1 wherein $R_1$ is independently selected from a $C_2$ up to $C_8$ alkyl, and an alkyl having a substituent selected from the group consisting of a carboxyl, acetyl, amido and hydroxy substituents, $R_2$ is independently selected from a $C_1$ up to $C_4$ alkyl or substituted alkyl.

5. The composition according to claim 3 wherein $R_1$ and $R_2$ cooperate to form a 5-, 6- or 7-membered ring, and the combination of $R_1$ and $R_2$ is selected from the group consisting of a saturated or unsaturated 4, 5 or 6 atom bridging species selected from the group consisting of alkylene, alkenylene, —O—, —S—, —C(O)— and —N(R)— containing alkylene moieties, wherein R is hydrogen or a lower alkyl moiety.

6. A method for the in vivo reduction of nitric oxide levels in a subject, said method comprising administering to the subject an effective amount of a composition comprising i. a pharmaceutically acceptable carrier, ii. a compound having the structure (I) as follows:

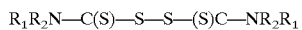

$$R_1R_2N-C(S)-S-S-(S)C-NR_2R_1 \quad (I)$$

wherein:

each of $R_1$ and $R_2$ is independently selected from a $C_1$ up to $C_{18}$ alkyl, substituted alkyl, a cycloalkyl, a substituted cycloalkyl, heterocyclic, a substituted heterocyclic, an alkenyl, a substituted alkenyl, an alkynyl, a substituted alkynyl, an aryl, a substituted aryl, an heteroaryl, a substituted heteroaryl, an alkylaryl, a substituted alkylaryl, an arylalkyl, and a substituted arylalkyl, or wherein $R_1$ and $R_2$ cooperate to form a 5-, 6- or 7-membered ring including N, $R_1$ and $R_2$ or $R_1$ or $R_2$ is a divalent moiety selected from the group consisting of an alkylene, a substituted alkylene, an oxyalkylene, a substituted oxyalkylene, an alkenylene, a substituted alkenylene, an arylene, a substituted arylene, an alkarylene, a substituted alkarylene, an aralkylene and a substituted aralkylene, wherein said divalent moiety serves as the same substituent for two dithiocarbamate structures, thereby linking said structures together so as to form a bis(dithiocarbamate), and iii. optionally, a reducing agent to reduce the disulfide bond in the dithiocarbamate.

wherein the composition is administered so as to bind free nitric oxide in the subject.

7. A method according to claim 6 wherein the nitric oxide levels are associated with a disease state selected from the group consisting of septic shock, ischemia, administration of cytokines, overexpression of cytokines, ulcers, gastritis, ulcerative colitis, Crohn's disease, diabetes, rheumatoid arthritis, asthma, Alzheimer's disease, Parkinson's disease, multiple sclerosis, cirrhosis, allograft rejection, transplant rejection, encephalomyelitis, meningitis, pancreatitis, peritonitis, vasculitis, lymphocytic choriomeningitis, glomerulonephritis, uveitis, glaucoma, blepharitis, chalazion, allergic eye disease, corneal ulcer, keratitis, cataract, retinal disorders, age-related macular degeneration, optic neuritis ileitis, inflammation induced by overproduction of inflammatory cytokines, hemorrhagic shock, anaphylactic shock, burn, infection leading to the overproduction of inflammatory cytokines induced by bacteria, virus, fungus, and parasites, hemodialysis, chronic fatigue syndrome, stroke, cancers, cardiovascular diseases associated with overproduction of inflammatory cytokines, heart disease, cardiopulmonary bypass, ischemic/reperfusion injury, ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, neuroblastoma, malaria, hematologic cancers, myelofibrosis, lung injury, graft-versus-host disease, head injury, CNS trauma, hepatitis, renal failure, chronic hepatitis C, liver disease, drug-induced lung injury, myasthenia gravis, transplant rejection and preservation, fertility enhancement, bacterial translocation, circulatory shock, traumatic shock, hemodialysis, hangover, and combinations of two or more thereof.

8. A method according to claim 7 wherein said species is selected from the group consisting of a cytokine, a cytokine receptor, an endotoxin, a platelet activating factor, a bradykinin, a bradykinin receptor, a bacteria, a parasite, a virus, a coagulation factor, an arachidonate metabolite, a nitric oxide synthase, nuclear factor kappa B, ultraviolet light, gamma ray irradiation, elevated temperature, and oxygen radicals.

9. A method according to claim 7 wherein said agent is selected from the group consisting of an inhibitor of cytokine synthesis/release, an anti-cytokine antibody, an anti-endotoxin antibody, a bradykinin antagonist, a synthetic peptide blocking bradykinin receptor, a bactericidal/permeability increasing protein, an inhibitor of the coagulation cascade, an antibody to platelet activating factor, an inhibitor of complement activation, an inhibitor of arachidonate metabolism, an inhibitor of nitric oxide synthase enzyme, is an immunosuppressor, a diabetic therapeutic agent, an anti-inflammatory, an anti-oxidant, an agent useful for stroke therapy, an agent useful for asthma therapy, an agent useful for cirrhosis therapy, an anti-cancer therapeutic, an anti-microbial therapeutic, an anti-fungal therapeutic, an anti-retroviral therapeutic, an agent useful for the treatment of opportunistic infections or malignancies, an agent useful for the treatment of Lupus erythmatosus, an agent useful for the treatment of uveitis, a thrombolytic agent, an antispasmodic agent, an antidiarrheal agent, useful for the treatment of constipation, useful for the treatment of constipation, an antihistamine, an agent useful for the treatment of constipation, and an agent useful for the treatment of Crohn's disease.

10. The method according to claim 7 wherein the disease state is diabetes.

11. The method according to claim 7 wherein the disease state is neurodegenerative disease.

12. The method according to claim 7 wherein the disease state is ulcerative colitis.

13. The method according to claim 7 wherein the disease state is Chron's disease.

14. The method according to claim 7 wherein the disease state is, inflammatory bowel disease.

15. The method according to claim 7 wherein the disease state is rheumatoid arthritis.

16. The method according to claim 7 wherein the disease state is stroke.

17. The method according to claim 7 wherein the disease state is hangover.

18. The method according to claim 7 wherein the disease state is hemodialysis.

19. The method according to claim 7 wherein the disease state is psoriasis.

20. The method according to claim 7 wherein the disease state is Alzheimer's disease.

21. The method according to claim 7 wherein the disease state is Parkinson's disease.

22. A method according to claim 8 wherein said inhibitor is an anti-cytokine receptor antibody.

23. A method according to claim 7 wherein the production of species which induce the expression of inducible nitric oxide synthase is associated with a condition selected from the group consisting of septic shock, ischemia, administration of cytokines, the overexpression of cytokines, ulcer, gastritis, ulcerative colitis, Crohn's disease, diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, glaucoma, blepharitis, chalazion, allergic eye disease, corneal ulcer, keratitis, cataract, retinal disorders, age-related macular degeneration, optic neuritis ileitis, inflammation caused by overproduction of cytokines, burn, infection leading to overproduction of cytokines, hemodialysis, chronic fatigue syndrome, stroke, cancers, heart disease, cardiopulmonary bypass, ischemic/reperfusion injury, ischemic/reperfusion associated with overproduction of inflammatory cytokines, adult respiratory distress syndrome, cachexia, myocarditis, autoimmune disorders, eczema, psoriasis, heart failure, atherosclerosis, dermatitis, urticaria, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, solid tumors, hematologic breast melanoma, carcinoma, cystic fibrosis, lung injury, graft-versus-host disease, head injury, CNS trauma, hepatitis, renal failure, chronic hepatitis C, liver disease, drug-induced lung injury, myasthenia gravis, transplant rejection and preservation, fertility enhancement, bacterial translocation, circulatory shock, hangover, traumatic shock, and combinations of two or more thereof.

24. A composition according to claim 1 further comprising at least one physiologically compatible compound selected from the group consisting of alpha-ketoglutaric acid, sodium thiosulfate, hydroxocobalamin, organophosphate antidote, therapeutic oxygen, resealed erythrocytes containing rhodanese and sodium thiosulfate, and a methemoglobin former.

25. A method according to claim 7 wherein the disease state is septic shock.

26. A method according to claim 7 wherein the disease state is ulcers.

27. A method according to claim 7 wherein the disease state is multiple sclerosis.

28. A method according to claim 7 wherein the disease state is cirrhosis.

29. A method according to claim 7 wherein the disease state is allograft rejection.

30. A method according to claim 7 wherein the disease state is allergic eye disease.

31. A method according to claim 7 wherein the disease state is corneal ulcer.

32. A method according to claim 7 wherein the disease state is hemorrhagic shock.

33. A method according to claim 7 wherein the disease state is hemodialysis.

34. A method according to claim 7 wherein the disease state is stroke.

35. A method according to claim 7 wherein the disease state is cancers.

36. A method according to claim 7 wherein the disease state is cardiopulmonary bypass.

37. A method according to claim 7 wherein the disease state is ischemic/reperfusion injury.

38. A method according to claim 7 wherein the disease state is adult respiratory distress syndrome.

39. A method according to claim 7 wherein the disease state is dermatitis.

40. A method according to claim 7 wherein the disease state is systemic lupus erythematosis.

41. A method according to claim 7 wherein the disease state is AIDS.

42. A method according to claim 7 wherein the disease state is migraine.

43. A method according to claim 7 wherein the disease state is gastrointestinal motility disorders.

44. A method according to claim 7 wherein the disease state is obesity.

45. A method according to claim 7 wherein the disease state is head injury.

46. A method according to claim 7 wherein the disease state is CNS trauma.

47. A method according to claim 7 wherein the disease state is hepatitis.

48. A method according to claim 7 wherein the disease state is renal failure.

49. A method according to claim 7 wherein the disease state is bacterial translocation.

50. A method according to claim 7 wherein the disease state is circulatory shock.

51. A method according to claim 7 wherein the disease state is hangover.

* * * * *